US007665238B2

(12) United States Patent
Majerowski

(10) Patent No.: US 7,665,238 B2
(45) Date of Patent: Feb. 23, 2010

(54) AIR FRESHENER WITH HOLDER

(75) Inventor: Amelia H. Majerowski, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 236 days.

(21) Appl. No.: 11/821,299

(22) Filed: Jun. 22, 2007

(65) Prior Publication Data

US 2007/0262166 A1  Nov. 15, 2007

Related U.S. Application Data

(63) Continuation-in-part of application No. 11/396,755, filed on Apr. 3, 2006, now Pat. No. 7,523,577.

(51) Int. Cl.
*G09F 1/12* (2006.01)
(52) U.S. Cl. .............................. 40/725; 40/768; 40/750; 392/390; 293/44; D23/366
(58) Field of Classification Search ............. 206/45.24, 206/45.28, 45.29, 461, 462, 467, 471, 764; 229/87.5, 92.8, 34, 60; 40/124.06, 124.11, 40/124.12, 672, 673, 745, 748, 750, 768, 40/800; 239/34, 60, 57, 58
See application file for complete search history.

(56) References Cited

U.S. PATENT DOCUMENTS

| 882,710 | A | 3/1908 | Pearsall |
|---|---|---|---|
| 886,840 | A | 5/1908 | Mueller |
| 1,068,621 | A | 7/1913 | Abraham |
| 1,204,934 | A | 11/1916 | Burford et al. |
| 1,261,133 | A | 4/1918 | Kidd |
| 1,802,999 | A | 4/1931 | Budd |
| 1,940,328 | A | 12/1933 | Schrotenboer |
| 2,268,529 | A | 12/1941 | Stiles |
| 2,469,656 | A | 5/1949 | Lienert |
| 2,550,954 | A | 5/1951 | Benedict |
| 2,577,320 | A | 12/1951 | Fenyo |

(Continued)

FOREIGN PATENT DOCUMENTS

EP    1082970 A1    3/2001

(Continued)

OTHER PUBLICATIONS

PCT/US2008/007642 International Search Report and Written Opinion dated Mar. 12, 2009.
http://www.glade.com/piso.asp.
http://www.glade.com/plugins.asp.
http://www.airwick.us/product page/product.html.

(Continued)

*Primary Examiner*—Lesley Morris
*Assistant Examiner*—Shin Kim

(57) ABSTRACT

A device adapted to discharge a volatile material includes a display frame having a front face and a rear face and an opening disposed in the rear face. The device further includes a dispenser disposed within the display frame. The dispenser includes a blister that holds a volatile material and a permeable membrane that extends across an open end of the blister. The rear face includes an integral foot member connected to an upper portion of the display frame at a hinge and the integral foot member is actuable between first and second states about the hinge. Further, the permeable membrane is disposed adjacent the rear face and regulates release of the volatile material therethrough.

19 Claims, 17 Drawing Sheets

U.S. PATENT DOCUMENTS

| | | |
|---|---|---|
| 2,579,715 A | 12/1951 | Wilson et al. |
| D169,871 S | 6/1953 | Speer et al. |
| 2,779,624 A | 1/1957 | Friedman |
| 2,840,689 A | 6/1958 | Kazor |
| 3,178,844 A | 4/1965 | Christian |
| 3,424,380 A | 1/1969 | Curran |
| 3,540,146 A | 11/1970 | Watkins |
| 3,544,007 A | 12/1970 | Bordman |
| 3,558,055 A | 1/1971 | Storchheim |
| 3,570,160 A | 3/1971 | Spertus |
| 3,638,343 A * | 2/1972 | West .................. 40/124.06 |
| 3,705,541 A * | 12/1972 | Kindig ....................... 396/31 |
| 3,741,711 A | 6/1973 | Bryant |
| 3,790,081 A | 2/1974 | Thornton et al. |
| 3,804,330 A | 4/1974 | Miller, Jr. et al. |
| 3,822,495 A | 7/1974 | Ohfuji |
| 3,948,445 A | 4/1976 | Andeweg |
| D243,402 S | 2/1977 | Irving |
| 4,009,384 A | 2/1977 | Holland |
| 4,055,672 A | 10/1977 | Hirsch |
| D247,573 S | 3/1978 | Schimanski |
| 4,101,720 A | 7/1978 | Taylor et al. |
| 4,157,787 A | 6/1979 | Schwartz |
| 4,158,440 A | 6/1979 | Sullivan et al. |
| 4,161,283 A * | 7/1979 | Hyman ....................... 239/55 |
| 4,165,573 A | 8/1979 | Richards |
| 4,170,080 A | 10/1979 | Bergh et al. |
| 4,173,604 A | 11/1979 | Dimacopoulos |
| 4,184,099 A | 1/1980 | Lindauer et al. |
| 4,254,910 A | 3/1981 | Martin |
| 4,285,468 A | 8/1981 | Hyman |
| D260,503 S | 9/1981 | Stangarone |
| 4,293,095 A | 10/1981 | Hamilton et al. |
| 4,314,915 A | 2/1982 | Wiegers et al. |
| D263,334 S | 3/1982 | Schimanski |
| 4,327,056 A | 4/1982 | Gaiser |
| D269,838 S | 7/1983 | Altonga |
| 4,411,829 A | 10/1983 | Schulte/Elte et al. |
| D271,359 S | 11/1983 | Le |
| 4,434,306 A | 2/1984 | Kobayashi et al. |
| D275,223 S | 8/1984 | Marxen |
| D275,700 S | 9/1984 | Marxen |
| 4,476,171 A | 10/1984 | Takeuchi |
| 4,493,011 A | 1/1985 | Spector |
| D279,146 S | 6/1985 | McCaffrey |
| D280,363 S | 9/1985 | Wisecup, Jr. |
| 4,549,250 A | 10/1985 | Spector |
| 4,580,581 A | 4/1986 | Reece et al. |
| D288,003 S | 1/1987 | Hoyt |
| 4,634,614 A | 1/1987 | Holzner |
| 4,695,435 A | 9/1987 | Spector |
| 4,714,984 A | 12/1987 | Spector |
| 4,720,409 A | 1/1988 | Spector |
| D296,957 S | 8/1988 | Gordon et al. |
| 4,762,275 A | 8/1988 | Herbert et al. |
| 4,781,895 A | 11/1988 | Spector |
| 4,794,714 A | 1/1989 | Weisgerber |
| 4,809,912 A | 3/1989 | Santini |
| 4,814,212 A | 3/1989 | Spector |
| 4,849,606 A | 7/1989 | Martens, III et al. |
| 4,874,129 A | 10/1989 | DiSapio et al. |
| 4,883,692 A | 11/1989 | Spector |
| D305,703 S | 1/1990 | Wang |
| 4,898,328 A | 2/1990 | Fox et al. |
| 4,913,349 A | 4/1990 | Locko |
| 4,917,301 A | 4/1990 | Munteanu |
| 4,921,636 A | 5/1990 | Traas |
| 4,939,858 A | 7/1990 | Dailey |
| 4,953,700 A * | 9/1990 | DeDino .................. 206/704 |
| 4,959,087 A | 9/1990 | Kappernaros |
| 4,993,177 A | 2/1991 | Hudson |
| 4,995,555 A | 2/1991 | Woodruff |
| D320,266 S | 9/1991 | Kunze |
| 5,060,858 A | 10/1991 | Santini |
| D325,077 S | 3/1992 | Kearnes |
| 5,148,983 A | 9/1992 | Muniz |
| 5,148,984 A | 9/1992 | Bryson et al. |
| 5,163,616 A | 11/1992 | Bernarducci et al. |
| 5,170,886 A | 12/1992 | Holzner |
| 5,219,121 A | 6/1993 | Fox et al. |
| 5,230,867 A | 7/1993 | Kunze et al. |
| D339,238 S | 9/1993 | Hamilton |
| D339,242 S | 9/1993 | Sontag et al. |
| 5,247,745 A | 9/1993 | Valentino |
| 5,249,380 A * | 10/1993 | Fast ............................ 40/672 |
| 5,255,456 A * | 10/1993 | Franklin ................ 40/124.191 |
| 5,259,555 A | 11/1993 | Kiefer |
| 5,282,553 A * | 2/1994 | Ibled .......................... 223/85 |
| 5,297,679 A * | 3/1994 | Rondone et al. ............ 206/468 |
| 5,297,732 A | 3/1994 | Hahn |
| D346,068 S | 4/1994 | White |
| 5,304,358 A | 4/1994 | Hoyt et al. |
| 5,334,361 A | 8/1994 | Rafaelides et al. |
| 5,361,521 A * | 11/1994 | Burtch ........................ 40/750 |
| 5,361,522 A | 11/1994 | Green |
| 5,367,802 A | 11/1994 | Rosenberg |
| D354,627 S | 1/1995 | Rowan |
| 5,395,047 A | 3/1995 | Pendergrass |
| 5,402,517 A | 3/1995 | Gillett et al. |
| D358,037 S | 5/1995 | Monroe |
| D360,461 S | 7/1995 | Gillespie |
| 5,439,100 A | 8/1995 | Gordon et al. |
| D361,896 S | 9/1995 | Bramley et al. |
| 5,462,006 A | 10/1995 | Thiruppathi |
| 5,478,505 A | 12/1995 | McElfresh |
| D366,107 S | 1/1996 | Shaffer |
| 5,503,332 A | 4/1996 | Glenn |
| D369,473 S | 5/1996 | Gluck |
| 5,529,243 A | 6/1996 | Hoyt et al. |
| D372,797 S | 8/1996 | Ilaria et al. |
| 5,556,192 A | 9/1996 | Wang |
| D374,777 S | 10/1996 | Agam |
| D376,002 S | 11/1996 | Upson |
| D376,420 S | 12/1996 | Rymer |
| D376,914 S | 12/1996 | Waszkiewicz |
| D380,822 S | 7/1997 | Decker et al. |
| 5,647,052 A | 7/1997 | Patel et al. |
| 5,651,942 A | 7/1997 | Christensen |
| D383,613 S | 9/1997 | Handler |
| D384,821 S | 10/1997 | Sugar |
| 5,679,334 A | 10/1997 | Semoff et al. |
| 5,711,955 A | 1/1998 | Karg |
| 5,716,000 A | 2/1998 | Fox |
| D392,031 S | 3/1998 | Miller |
| D392,032 S | 3/1998 | Zaragoza et al. |
| 5,735,460 A | 4/1998 | Eisenbraun |
| 5,744,106 A | 4/1998 | Eagle |
| 5,749,519 A | 5/1998 | Miller |
| 5,749,520 A | 5/1998 | Martin et al. |
| 5,782,409 A | 7/1998 | Paul |
| 5,788,155 A | 8/1998 | Martin et al. |
| 5,804,264 A | 9/1998 | Bowen |
| D399,298 S | 10/1998 | Whitehead |
| D401,767 S | 12/1998 | Leung |
| 5,845,847 A | 12/1998 | Martin et al. |
| D405,473 S | 2/1999 | Tikhonski et al. |
| D405,961 S | 2/1999 | Stangl |
| 5,875,968 A | 3/1999 | Miller et al. |
| 5,885,701 A | 3/1999 | Berman et al. |
| D407,809 S | 4/1999 | Hammond |
| 5,899,382 A | 5/1999 | Hayes et al. |
| 5,950,922 A | 9/1999 | Flinn |
| 5,961,043 A * | 10/1999 | Samuelson et al. ............ 239/54 |
| 5,975,427 A * | 11/1999 | Harries ........................ 239/34 |

| | | |
|---|---|---|
| 6,031,967 A | 2/2000 | Flashinski et al. |
| D424,812 S | 5/2000 | Kacius |
| 6,065,687 A | 5/2000 | Suzuki et al. |
| 6,106,786 A | 8/2000 | Akahoshi |
| 6,109,537 A | 8/2000 | Heath |
| D431,075 S | 9/2000 | Barraclough |
| 6,112,496 A | 9/2000 | Hugus et al. |
| 6,144,801 A | 11/2000 | Lehoux et al. |
| 6,152,379 A | 11/2000 | Sorgenfrey |
| 6,154,607 A | 11/2000 | Flashinski et al. |
| D435,100 S | 12/2000 | Pesu et al. |
| D437,404 S | 2/2001 | Wu |
| D439,964 S | 4/2001 | Wu |
| D441,441 S | 5/2001 | Upson |
| D445,262 S | 7/2001 | Rowan |
| 6,254,248 B1 | 7/2001 | McAuley et al. |
| 6,254,836 B1 | 7/2001 | Fry |
| D451,990 S | 12/2001 | Millet |
| 6,328,935 B1 | 12/2001 | Buccellato |
| D453,561 S | 2/2002 | Nelson |
| 6,354,710 B1 | 3/2002 | Nacouzi |
| 6,358,577 B1 | 3/2002 | Bowen et al. |
| 6,363,734 B1 | 4/2002 | Aoyagi |
| 6,367,706 B1 | 4/2002 | Putz |
| D456,620 S | 5/2002 | Vincent |
| D456,888 S | 5/2002 | Buthier |
| D461,006 S | 7/2002 | Buthier |
| D461,393 S | 8/2002 | Aubert |
| 6,435,423 B2 | 8/2002 | Hurry et al. |
| 6,478,440 B1 | 11/2002 | Jaworski et al. |
| 6,484,425 B1 | 11/2002 | Hirsch |
| 6,526,636 B2 | 3/2003 | Bernhardt |
| 6,548,015 B1 | 4/2003 | Stubbs et al. |
| 6,555,068 B2 | 4/2003 | Smith |
| D476,726 S | 7/2003 | Rosenberg |
| 6,610,254 B1 | 8/2003 | Furner et al. |
| D479,742 S | 9/2003 | Hollingsworth |
| 6,618,974 B2 | 9/2003 | Szalay |
| 6,627,857 B1 | 9/2003 | Tanner et al. |
| D480,221 S | 10/2003 | Luciano |
| D481,113 S | 10/2003 | Groene et al. |
| 6,631,852 B1 | 10/2003 | O'Leary |
| 6,638,591 B2 | 10/2003 | Bowen et al. |
| D481,785 S | 11/2003 | Koike |
| 6,643,967 B1 | 11/2003 | Bloom |
| 6,648,239 B1 | 11/2003 | Myny et al. |
| 6,663,838 B1 | 12/2003 | Soller et al. |
| D485,607 S | 1/2004 | Wu |
| 6,691,870 B1 * | 2/2004 | Palm et al. ............... 206/462 |
| D487,308 S | 3/2004 | Engerant |
| 6,705,541 B2 | 3/2004 | Schuehrer et al. |
| 6,714,725 B2 | 3/2004 | Grone et al. |
| 6,722,578 B2 | 4/2004 | Skalitzky et al. |
| 6,730,311 B2 | 5/2004 | Maleeny et al. |
| 6,749,672 B2 | 6/2004 | Lynn |
| 6,790,436 B2 | 9/2004 | Williams et al. |
| 6,808,791 B2 | 10/2004 | Curro et al. |
| D498,524 S | 11/2004 | Morillas |
| D498,525 S | 11/2004 | Harbutt et al. |
| D498,836 S | 11/2004 | Morillas |
| 6,826,863 B1 | 12/2004 | Goodfellow |
| 6,871,430 B1 * | 3/2005 | Landolt ................ 40/124.12 |
| 6,889,840 B2 * | 5/2005 | Schein et al. ............. 206/704 |
| 6,998,581 B2 | 2/2006 | Currie |
| 7,028,917 B2 | 4/2006 | Buthier |
| 7,036,747 B2 | 5/2006 | Channer |
| 7,138,367 B2 | 11/2006 | Hurry et al. |
| 7,175,815 B2 | 2/2007 | Yamasaki et al. |
| 2003/0007887 A1 | 1/2003 | Roumpos et al. |
| 2003/0085297 A1 | 5/2003 | Huang |
| 2003/0089791 A1 | 5/2003 | Chen et al. |
| 2003/0094503 A1 | 5/2003 | Rymer et al. |
| 2003/0200690 A1 | 10/2003 | Galloway |
| 2004/0000596 A1 | 1/2004 | Cuthbert |
| 2004/0057975 A1 | 3/2004 | Maleeny et al. |
| 2004/0262418 A1 | 12/2004 | Smith et al. |
| 2005/0001337 A1 | 1/2005 | Pankhurst |
| 2005/0103880 A1 | 5/2005 | Taite |
| 2005/0145711 A1 | 7/2005 | Blondeau et al. |
| 2005/0196571 A1 | 9/2005 | Penny et al. |
| 2006/0000920 A1 | 1/2006 | Leonard |

FOREIGN PATENT DOCUMENTS

| | | |
|---|---|---|
| EP | 0 645 081 | 7/2001 |
| EP | 1295613 A | 3/2003 |
| EP | 1 346 734 | 9/2003 |
| GB | 2158356 A | 11/1985 |
| GB | 2 254 558 | 10/1992 |
| GB | 3003643 | 11/2002 |
| GB | 3003644 | 6/2003 |
| GB | 3005817 | 7/2003 |
| GB | 3007046 | 9/2003 |
| GB | 3007049 | 9/2003 |
| GB | 3007052 | 9/2003 |
| GB | 3007053 | 9/2003 |
| GB | 3007054 | 9/2003 |
| GB | 3007055 | 9/2003 |
| GB | 3007056 | 9/2003 |
| GB | 3007057 | 9/2003 |
| GB | 3007233 | 9/2003 |
| GB | 3007045 | 10/2003 |
| GB | 3012024 | 2/2004 |
| GB | 3012025 | 2/2004 |
| GB | 3012026 | 2/2004 |
| GB | 3007048 | 10/2005 |
| JP | HA05015803 | 8/1993 |
| JP | 08-241039 | 9/1996 |
| JP | 9-84863 | 3/1997 |
| JP | D1027932 | 9/1998 |
| JP | 10-263068 | 10/1998 |
| JP | D1195937 | 2/2004 |
| NL | 000194709/0001 | 9/2004 |
| NL | 000205661/0001 | 10/2004 |
| NL | 000252358/0001 | 2/2005 |
| NL | 000252366/0001 | 2/2005 |
| WO | WO 96/33605 | 10/1996 |
| WO | WO97/22370 A | 6/1997 |
| WO | WO 00/23121 | 4/2000 |
| WO | WO 03/068276 | 8/2003 |
| WO | WO 2007/096432 | 8/2007 |
| WO | 2007120487 A | 10/2007 |

OTHER PUBLICATIONS http://www.racerwheel.com/tcr/cz/103.html.
http://www.racerwheel.com/tcr/cz/102a.html.
http://www.giftsandgadgetsonline.com/ioairfrwilif.html.
http://www.allproducts.com/gift/sundeal/02/ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ/201ionicfreshener.html.
http://www.buylighting.com/Odor eliminating light bulbs.html.
Int'l Search Report and Written Opinion Appl. No. PCT/US2005/023226 dated Sep. 12, 2005.
Int'l Search Report and Written Opinion Appl. No. PCT/US2005/023228 dated Nov. 3, 2005.
International Search Report in PCT/US2007/001568 dated Jun. 29, 2007.
International Search Report and Written Opinion in PCT/US2007/008035 dated Aug. 2, 2007.
International Search Report & Written Opinion for PCT/US2007/008116 dated Nov. 26, 2007.

* cited by examiner

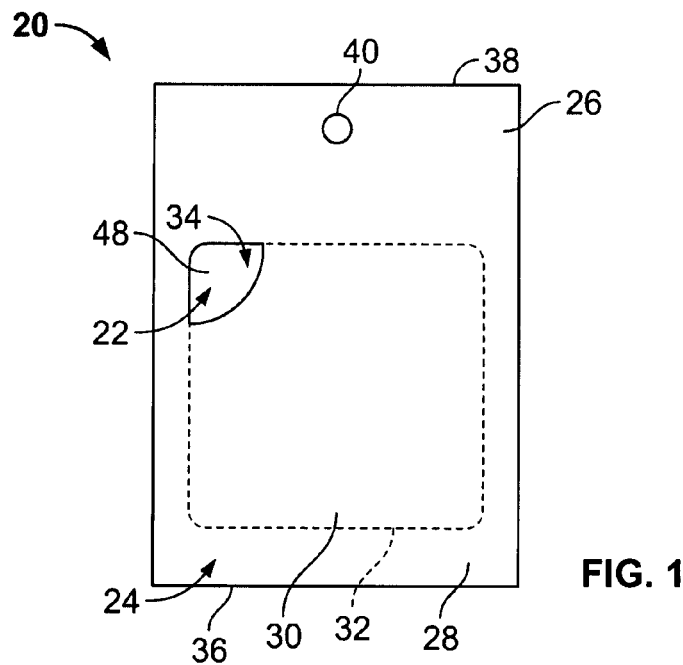
FIG. 1
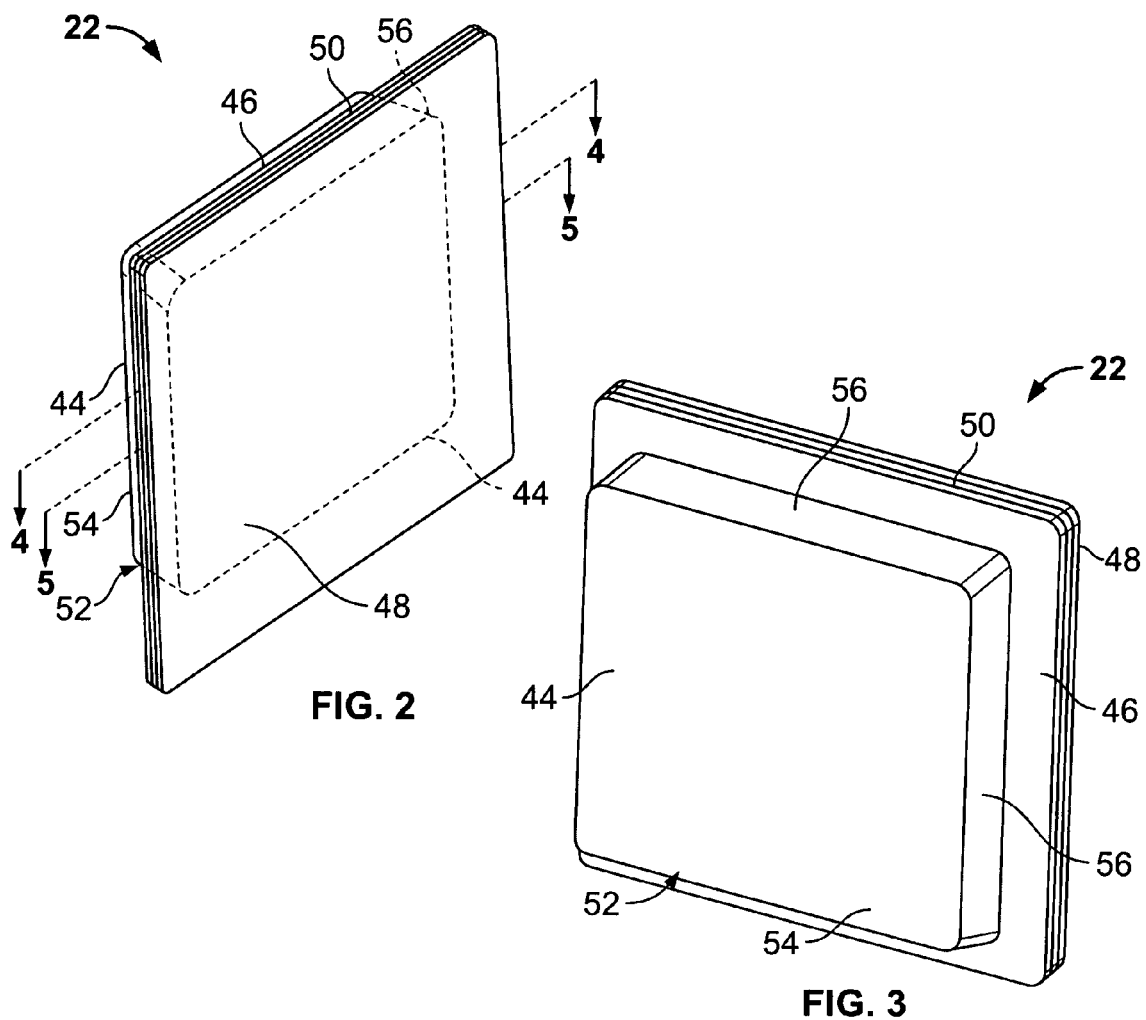
FIG. 2
FIG. 3

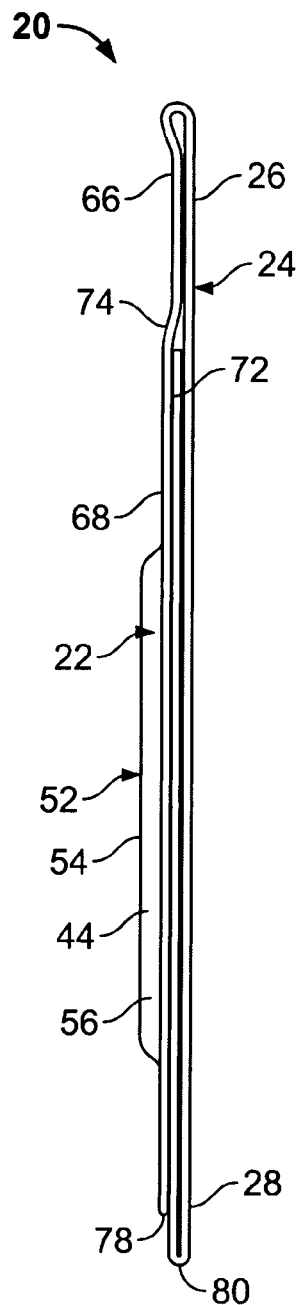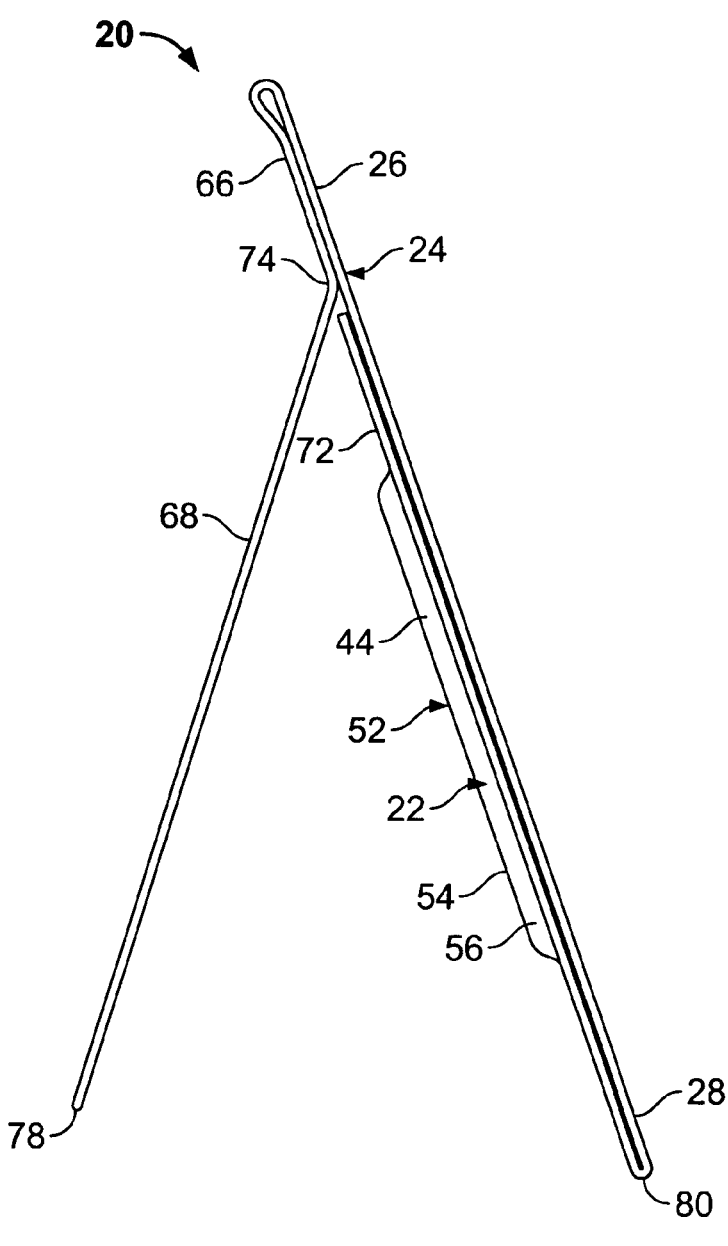
FIG. 8  FIG. 11

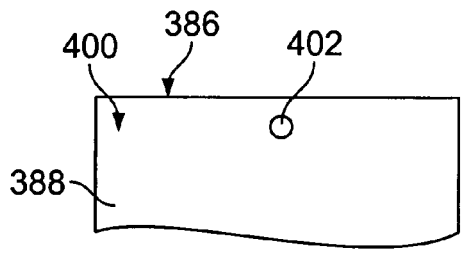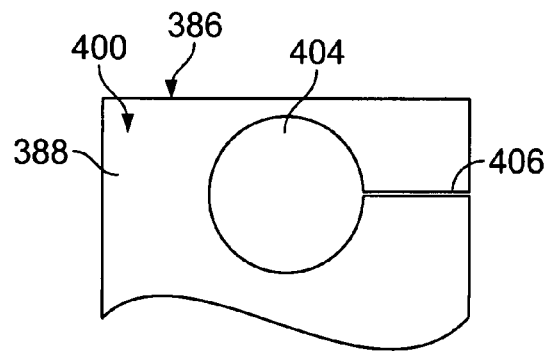
FIG. 29     FIG. 30
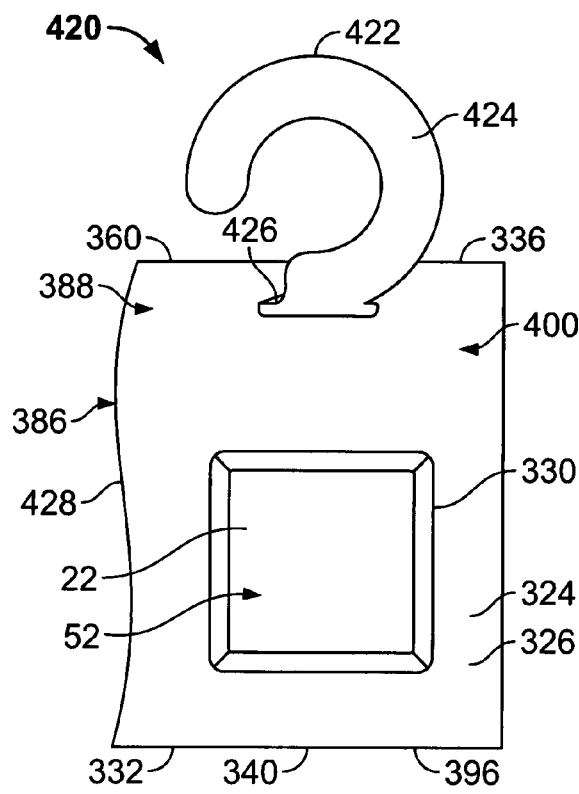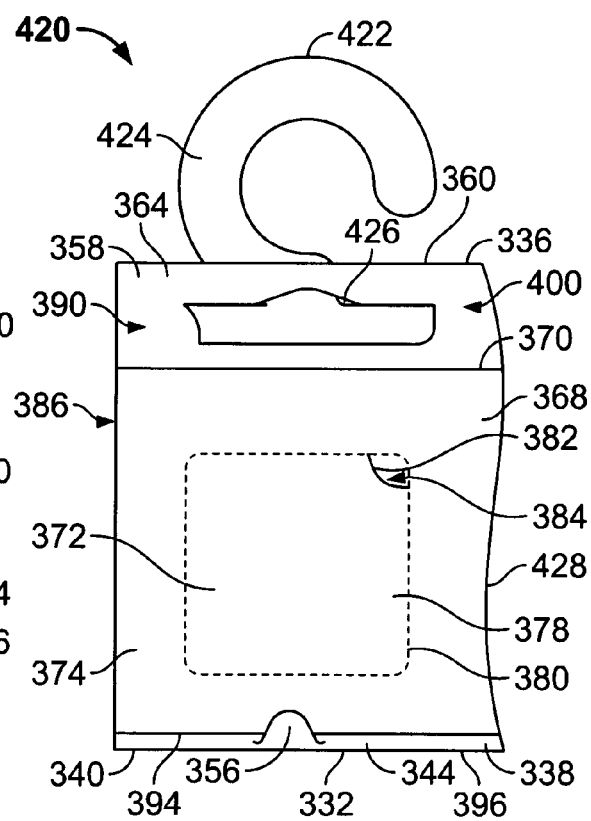
FIG. 31A     FIG. 31B

AIR FRESHENER WITH HOLDER

CROSS REFERENCE TO RELATED APPLICATIONS

This application is a continuation-in-part of U.S. patent application Ser. No. 11/396,755, filed Apr. 3, 2006 now U.S. Pat. No. 7,523,577. The aforesaid application is hereby incorporated by reference herein in its entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispensing system, and more particularly, to a volatile material dispenser in combination with an adjustable chipboard holder.

2. Description of the Background

Volatile material dispensers have been used to provide fragrances to office or home settings. One such dispenser is an ornamental design for a combined picture frame and potpourri holder. The design includes front and rear panels angled from each other. A recess is centered within the front panel to provide an area to insert a photograph. A bridge connects both the front and rear panels.

Another such ornamental design for a dispenser includes a combined air freshener and picture frame. The frame includes front and rear faces, wherein the front face includes two rectangular stepped portions extending outwardly therefrom and the rear face is planar. An opening extends through the front and rear faces adjacent an upper portion of the frame.

Yet another dispenser includes first and second panels. A base joins the first and second panels to provide a platform to support the device in a tent configuration. The second side panel has a tab extending therefrom. Means are provided to capture the tab that is associated with the first side panel. An opening in one of the side panels is provided for mounting a volatile material filled reservoir.

SUMMARY OF THE INVENTION

According to one embodiment, a device adapted to discharge a volatile material includes a display frame having a front face and a rear face and an opening disposed in the rear face. The device further includes a dispenser disposed within the display frame. The dispenser includes a blister that holds a volatile material and a permeable membrane that extends across an open end of the blister. The rear face includes an integral foot member connected to an upper portion of the display frame at a hinge and the integral foot member is actuable between first and second states about the hinge. Further, the permeable membrane is disposed adjacent the rear face and regulates release of the volatile material therethrough.

According to another embodiment, a dispensing system includes a frame having a front segment and a rear segment and an opening disposed in the rear segment. The dispensing system further includes a dispenser disposed within the frame. The dispenser comprises a blister holding a volatile material and a permeable membrane extending across an open end of the blister. Further, a value-added feature is included with the frame. The rear segment includes an integral foot connected to an upper portion of the frame at a hinge and the integral foot is actuable between first and second states about the hinge. In addition, the permeable membrane is disposed facing toward the rear segment.

According to yet another embodiment, a substantially flat blank adapted for assembly into a dispensing system includes a first wall segment defining a first opening and a second wall segment hingedly connected to a first end of the first wall segment about a first fold line. The second wall segment includes a first removable face extending across a second opening. The blank further includes a third wall segment hingedly connected to a second end of the first wall segment about a second fold line and a fourth wall segment hingedly connected to an end of the third wall segment about a third fold line. The fourth wall segment further includes a second removable face extending across a third opening. The first and second openings are adapted to align with one another in an assembled state.

BRIEF DESCRIPTION OF THE DRAWINGS

Other aspects and advantages of the present invention will become apparent upon reading the following detailed description and upon reference to the drawings in which:

FIG. 1 is front elevational view of the dispensing system in a first state that includes a frame and a dispenser;

FIG. 2 is an front isometric view of the dispenser of FIG. 1;

FIG. 3 is a rear isometric view of the dispenser of FIG. 1;

FIG. 8 is a side elevational view of the dispensing system of FIG. 1;

FIG. 11 is a side elevational view of the dispensing system of FIG. 9;

FIG. 29 is another embodiment of an upper portion of any of the dispensing systems described herein;

FIG. 30 is yet another embodiment of an upper portion of any of the dispensing systems described herein;

FIG. 31A is a front elevational view of a further embodiment of the fourth dispensing system similar to the one shown in FIG. 21 having a contoured side and a hook;

FIG. 31B is a rear elevational view of the dispensing system depicted in FIG. 31A;

DETAILED DESCRIPTION OF THE INVENTION

Figure 4:
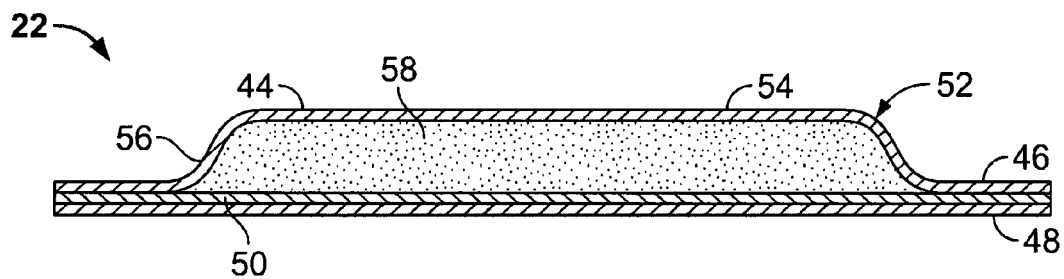
FIG. 4 is a cross-sectional view of the dispenser of FIG. 2 along the lines 4-4 in a first condition.

Referring to FIG. 1, a volatile material dispensing system 20 is illustrated. The dispensing system 20 includes a volatile material dispenser 22 and a display frame 24. The frame 24 is operable between first and second states to provide a user various manners of utilizing the present dispensing system 20.

FIG. 1 depicts the display frame 24 in the first state. A front face 26 of the display frame 24 comprises a first wall portion 28. The first wall portion 28 is substantially rectangular in shape and has a width of about 3.5 in. and a height of about 5 in. A cover 30 is provided within the front wall portion 28 and attached thereto by a perforated section 32 about a periphery of the cover 30. The cover 30 is substantially square except for an arcuately shaped portion that has been removed from an upper corner of the cover 30. The removed portion defines a slot 34. The cover 30 is substantially centered about the width of the front face 26 and is directed closer to a bottom end 36 of the display frame 24 than a top end 38 thereof. A hole 40 is disposed within the first wall portion 28 adjacent the top end 38.

The cover 30 overlies the dispenser 22 further illustrated in FIGS. 2-5. With reference to FIGS. 2 and 3, the dispenser 22 or cartridge comprises a blister 44, a peripheral flange 46, and an impermeable laminate 48 releasably adhered to the blister 44 and the flange 46. The blister 44 includes a non-porous permeable membrane 50 and a cup-shaped structure 52 or reservoir. The cup-shaped structure 52 includes a bottom wall 54 and four side walls 56 that in conjunction with the permeable membrane 50 act as a sealed reservoir to contain a volatile material 58 (shown in FIGS. 4 and 5). Illustratively, the cup-shaped structure 52 and the permeable membrane 50 are formed from clear and/or translucent materials, thereby allowing the volatile material 58 to be visible therethrough. The peripheral flange 46 is planar and is coupled to and extends outwardly from top edges of the cup-shaped structure 52. In one embodiment, the peripheral flange 46 extends outwardly from upper edges of the side walls 56 and is integrally formed therewith. The present dispenser 22 and the volatile material 58 are similar to those described in U.S. Pat. No. 7,213,770, the disclosure of which is herein incorporated by reference in its entirety.

FIG. 4 illustrates the dispenser 22 in a first condition. The dispenser 22 is completely or substantially full in the first condition, i.e., little or no volatile material 58 has diffused through the permeable membrane 50 because the impermeable laminate 48 has not been removed from the blister 44. There is substantially no diffusion of the volatile material 58 when the dispenser 22 is filled and the impermeable laminate 48 covers the permeable membrane 50. Illustratively, the impermeable laminate 48 is removed from the blister 44 by a user grasping an end of the impermeable laminate 48 and peeling it off the blister 44. A tab 60, extension, or other means for grasping may be included as an extension of the impermeable laminate 48 to aid in removal of same. The extension may be at the corners, ends, and/or on the surface of the impermeable laminate 48.

Figure 5:
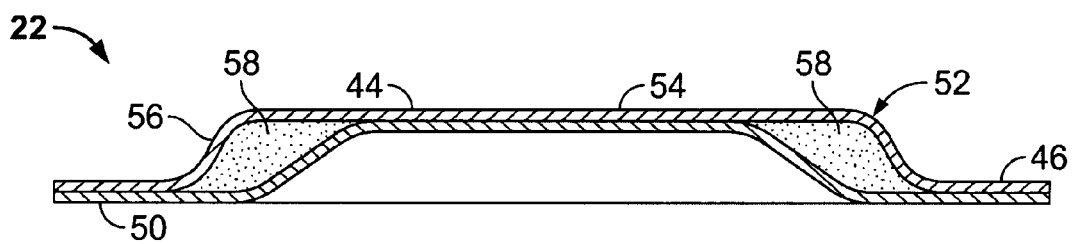
FIG. 5 is a cross-sectional view of the dispenser of FIG. 2 along the lines 5-5 in a second condition.

Following removal of the impermeable laminate 48, the dispenser 22 begins to transition from a full or first condition (FIG. 4) to an empty or second condition (FIG. 5). There may be a small amount of the volatile material 58 that remains in the blister 18 and the dispenser 22 will still be considered to have reached the second condition. As the volatile material 58 diffuses through the permeable membrane 50, the permeable membrane 50 slowly collapses upon the bottom wall 54. With reference to FIG. 5, following diffusion of the volatile material 58 across the permeable membrane 50 there is less volatile material 58 contained within the dispenser 22. Substantially no new air enters the dispenser 22 subsequent to diffusion of the volatile material 58. The result of this is a pressure gradient across the permeable membrane 50, with a higher pressure existing in the ambient air than the pressure in the dispenser 22. The pressure gradient causes the ambient air to exert a net positive pressure upon the dispenser 22, which presses the permeable membrane 50 against the remaining volatile material 58 and ultimately the bottom wall 54.

Figure 6:
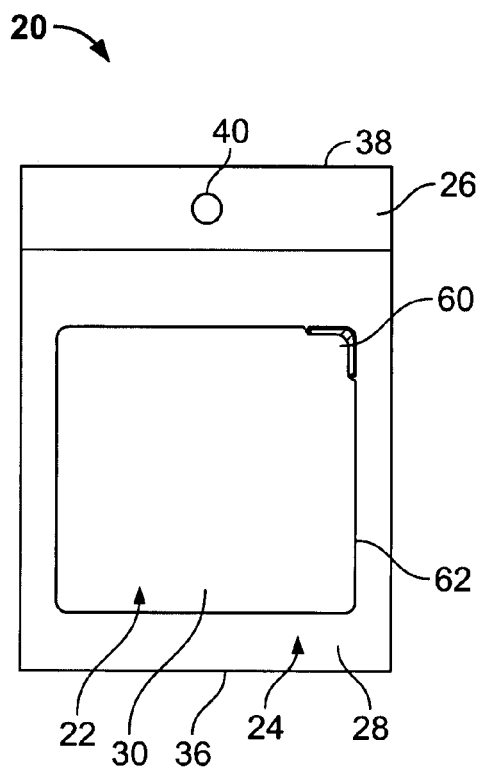
FIG. 6 is a front elevational view of the dispensing system of FIG. 1 with a front cover removed therefrom.

With reference again to FIG. 1, a portion of the impermeable laminate 48 is visible through the slot 34. The dispensing system 20 is activated by removing the cover 30 from the display frame 24, such as is depicted in FIG. 6. The cover 30 is removed by grabbing a portion of the cover 30 within the slot 34 and pulling the cover 30 outwardly away from the display frame 24. When a sufficient force is exerted upon the cover 30, same will tear away from the first wall portion 28 and provide a substantially square opening 62. The opening 62 in one embodiment has length and width measurements of about 2.876 in. The impermeable laminate 48 is viewable and accessible through the opening 62. The impermeable laminate 48 extends a distance substantially coterminous with a width and height of the opening 62. The impermeable laminate 48 is removed by grasping a portion of the laminate 48, such as the tab 60, and pulling the laminate 48 off of the blister 44. Removal of the impermeable laminate 48 allows the dispenser 22 to transition from the first condition (FIG. 4) to the second condition (FIG. 5), thereby allowing for the volatile material 58 to be dispersed into the atmosphere.

Figure 7:
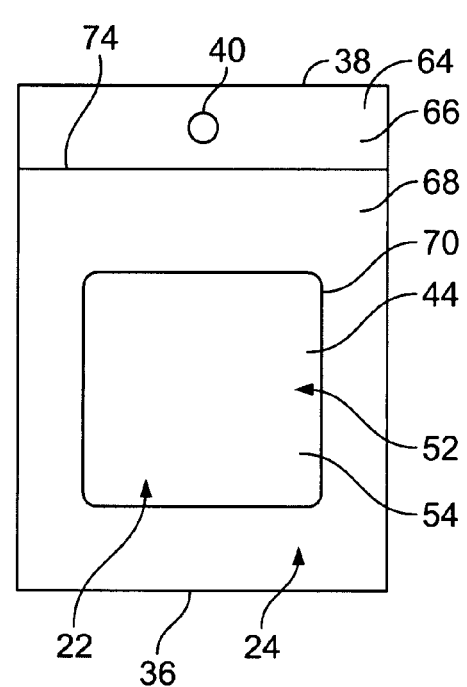
FIG. 7 is rear elevational view of the dispensing system of FIG. 1.
Figure 9:
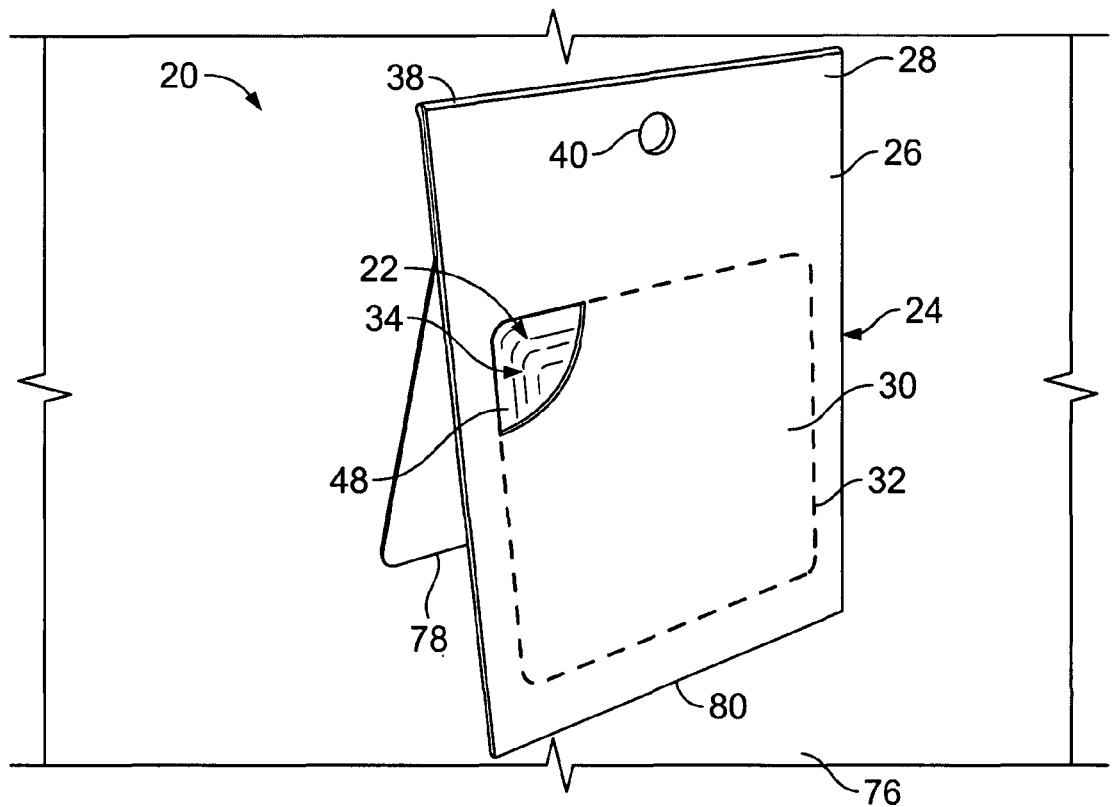
FIG. 9 is an front isometric view of the dispensing system of FIG. 1 in a second state.
Figure 10:
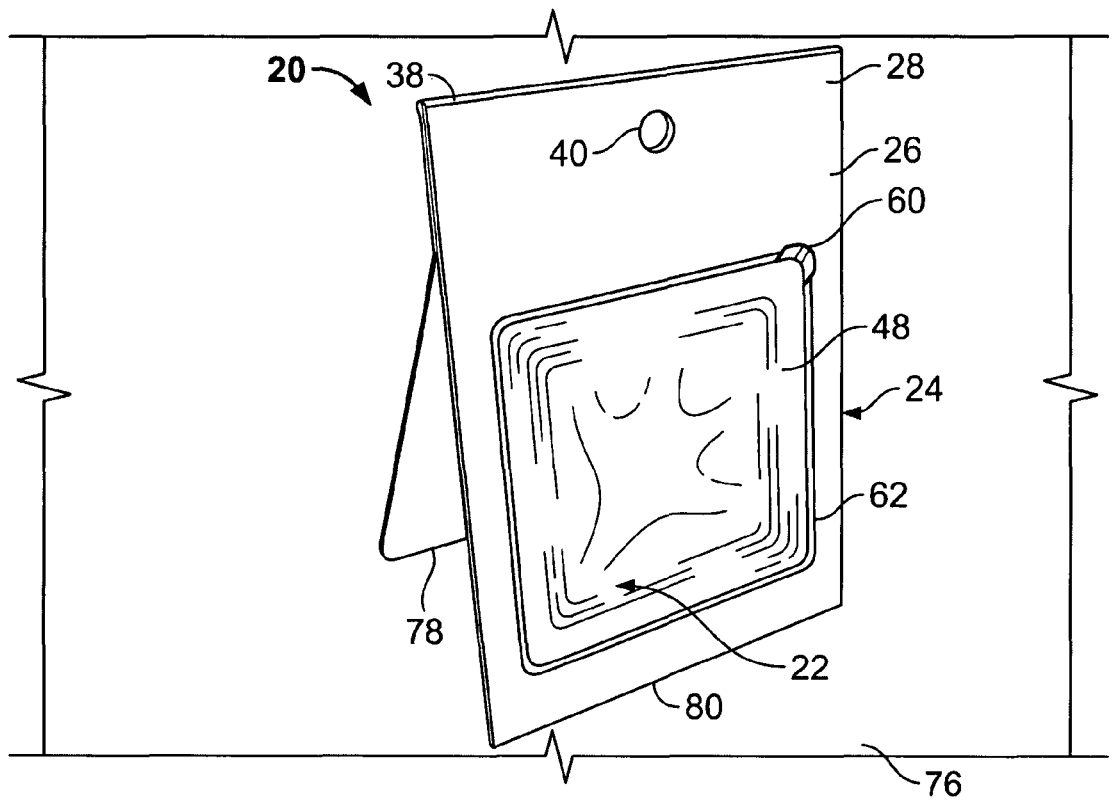
FIG. 10 is a front isometric view of the dispensing system of FIG. 9 with a front cover removed therefrom.

A rear face 64 of the display frame 24 is depicted in FIG. 7. The rear face 64 comprises second and third wall portions 66, 68, respectively. The second wall portion 66 is substantially rectangular in shape and has a width of about 3.5 in. and a height of about 1 in. The third wall portion 68 is integrally connected to the second wall portion 66 and has a width of about 3.5 in. and a height of about 4 in. A second opening 70 is provided within the third wall portion 66. The second opening 70 is substantially square-shaped and has length and width dimensions substantially equal to or greater than the length and width dimensions of the cup-shaped structure 52 of the blister 44. In one embodiment, the second opening 70 is dimensioned to be smaller than the opening 62 of the first wall portion 28 and has length and width measurements of about 2.313 in. The second opening 70 is centered about the width of the rear face 64 and is disposed closer to the bottom end 36 of the display frame 24 than the top end 38. The hole 40 extends through the second wall portion 66 adjacent the top end 38 of the display frame 24. The cup-shaped structure 52 protrudes through the second opening 70. In other embodiments, the cup-shaped structure 52 partially protrudes into the second opening 70 or is substantially aligned therewith. FIG. 8 provides a side elevational view that illustrates the extent to which the cup-shaped structure 52 extends through the second opening 70 in the present embodiment. The distance the cup-shaped structure 52 extends through the second opening 70 may be modified by adjusting the dimensions of the dispenser 22 and/or the display frame 24. For example, one or more of the first wall portion 28, the second wall portion 66, the third wall portion 68, or a fourth wall portion 72 may be manufactured from a material having a different thickness to adjust the degree to which the cup-shaped structure 52 extends though the second opening 70.

The dispensing system of FIGS. 1 and 6-11 depict the dispensing system 20 in the first state. The first state is characterized by having the first, second, third, and fourth wall portions 28, 66, 68, 72 disposed in a substantially parallel manner to each other. Portions of the dispenser 22, such as the bottom wall 54 and the impermeable laminate 48, are also parallel to the first, second, third, and fourth wall portions 28, 66, 68, 72. Typically, a cord or other member is strung through the hole 40 and the dispensing system 20 is hung from a support structure (not shown). In a different embodiment, the dispensing system 20 is propped against a wall or other surface or may be laid upon a support surface. There are numerous manners of deploying the dispensing system 20 in the first state that users may employ.

Figure 12:
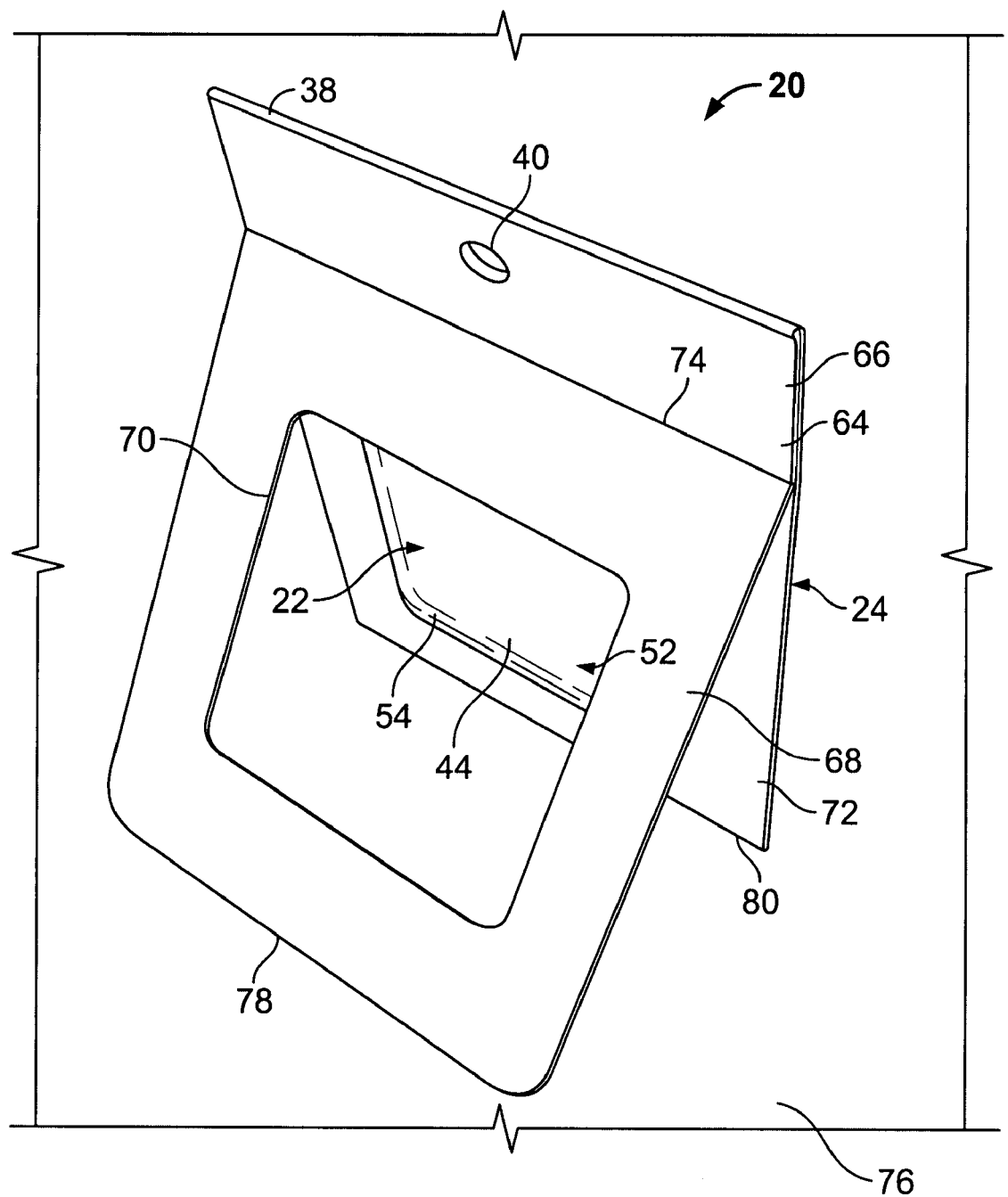
FIG. 12 is a rear isometric view of the dispensing system of FIG. 9.

Referring now to FIGS. 9-12, the dispensing system 20 is disposed in the second state. With particular reference to FIG. 12, the rear face 64 of the display frame 24 is shown. The third wall portion 68 is rotated about a hinge 74 to extend outwardly from the remaining portions of the display frame 24. In the second state, the cup-shaped structure 52 does not extend through the second opening 70 and is no longer aligned therewith. The third wall portion 68 acts as a support member or foot member to assist in propping up the dispensing system 20 from a support surface 76. FIG. 11 illustrates that the dispensing system 20 takes on a substantially inverted V-shape in the second state with the second wall portion 66 and portions of the first wall portion 28 extending therefrom at an angle. A bottom end 78 of the third wall portion 68 and a bottom end 80 of the combined first and fourth wall portions 28, 72 exert forces upon the support surface 76 to maintain the dispensing system 20 in an upright position in the second state.

The third wall portion 68 is actuable between the first state and a plurality of positions that define the second state. Prior to placing the dispensing system 20 in the second state, the third wall portion 68 is juxtaposed with the fourth wall portion 72 and substantially parallel therewith in a first position. The dispensing system is placed in the second state by rotating the third wall portion 68 about the hinge 74. Rotation of the third wall portion 68 causes same to be angled from the fourth wall portion 72 and placed in a second position. The third wall portion 68 may be angled anywhere between about 1 degree to about 180 degrees to place the dispensing system 20 in the second state. Illustratively, the angle of the third wall portion 68 is between about 20 degrees and about 70 degrees.

Regardless of whether the dispensing system 20 is in the first or second state, the permeable membrane 50 of the dispenser 22 is directed substantially away from the rear face 64 of the display frame 24. The volatile material 58 is therefore emitted into the atmosphere without obstruction, thereby allowing for more efficient diffusion of the volatile material 58. The permeable membrane 50 is also viewable from the front face 26 of the dispensing system 20. A user may therefore determine the level of the volatile material 58 remaining in the dispenser 22 without exercising great effort.

Figures 13, 14:
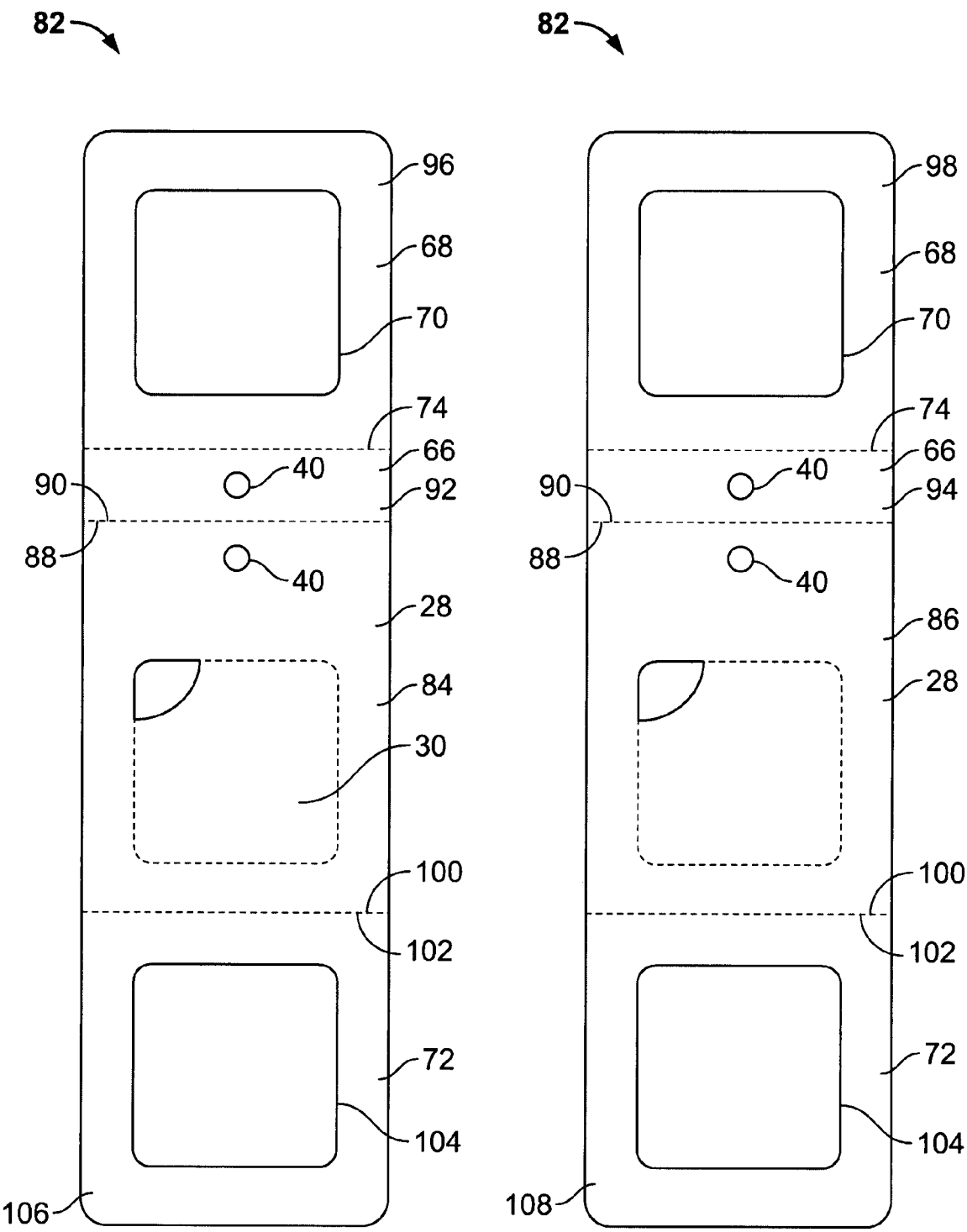
FIG. 13 is a plan view of a front side of a blank used to manufacture the dispensing system of FIGS. 1 and 6-12.
FIG. 14 is a plan view of a rear side of the blank of FIG. 13.

FIGS. 13 and 14 illustrate one type of blank 82 that may be used to manufacture the present dispensing system 20. The blank 82 may be manufactured from paperboard or the like and die cut into the appropriate shape. FIG. 13 depicts a front side 84 of the first wall portion 28 with the removable cover 30 and the hole 40. FIG. 14 depicts a rear side 86 of the first wall portion 28. The second wall portion 66 is attached to a first end 88 of the first wall portion 28 by a hinge 90 or a fold line. The second wall portion 66 also includes the hole 40 and front and rear sides 92, 94, respectively. The third wall portion 68 is attached to the opposite end of the second wall portion 66 at the hinge 74 or a fold line. The third wall portion 68 includes the second opening 70 and front and rear sides 96, 98, respectively. The fourth wall portion 72 is attached to a second end 100 of the first wall portion 28 by a hinge 102 or a fold line. The fourth wall portion 72 includes a third opening 104 similar in dimensions to the second opening 70 and front and rear sides 106, 108, respectively.

The dispensing system 20 is assembled by inserting the cup-shaped structure 52 of the dispenser 22, which is not shown in FIG. 13, through the third opening 104 from the rear side 108 of the fourth wall portion 72. The peripheral flange 46 of the dispenser 22 is hot sealed onto portions of the rear side 108 of the fourth wall portion 72 surrounding the third opening 104. The fourth wall portion 72 is rotated about the hinge 102 to position the rear side 108 of the fourth wall portion 72 substantially flush with the rear side 86 of the first wall portion 28. The rear side 108 of the fourth wall portion 72 and the rear side 86 of the first wall portion 28 are hot sealed together. When the fourth wall portion 72 is positioned in such a manner the impermeable laminate 48 of the dispenser 22 is centered behind the cover 30 of the first wall portion 28. The second wall portion 66 is folded about the hinge 90 so that the holes 40 are aligned. The rear side 94 of the second wall portion 66 is similarly hot sealed to the rear side 86 of the first wall portion 28. The remaining third wall portion 68 lies substantially flush against the fourth wall portion 72 so that the rear side 98 of the third wall portion 68 is juxtaposed against the front side 106 of the fourth wall portion 72.

Figure 15:
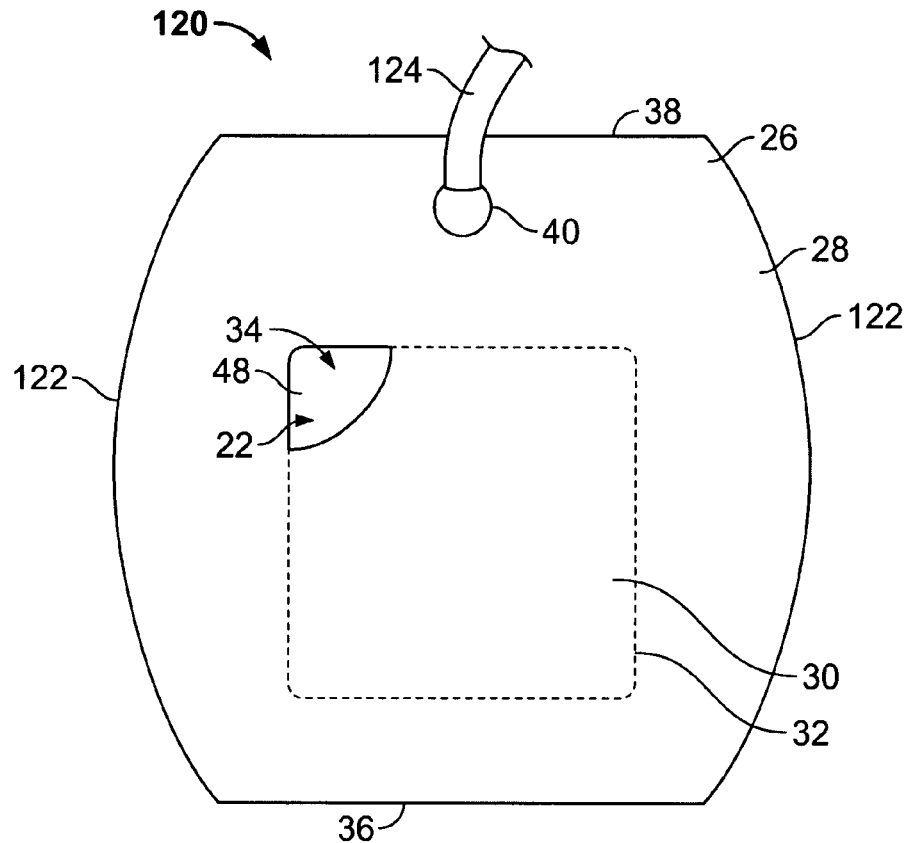
FIG. 15 is a front elevational view of a second dispensing system in a first state that includes a frame and a dispenser.
Figure 16:
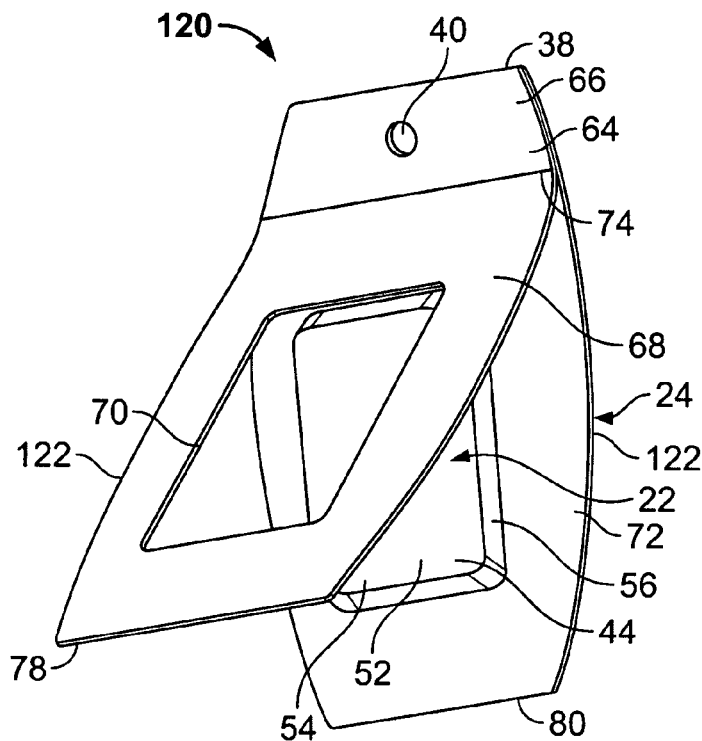
FIG. 16 is a rear isometric view of the second dispensing system of FIG. 15 in a second state.

The blank 82 may comprise any other type of paper based material or a different material such as plastic. Different materials such as plastics may be useful in humid environments that would otherwise be harmful to paper based materials. Further, portions of the blank 82 and the dispenser 22 may be adhered to one another by an adhesive or different type of glue. The display frame 24 itself may also be shaped in a decorative manner for aesthetic effect or provided with varying colors and/or pictures. FIGS. 15 and 16 depict one such dispensing system 120, wherein like reference numerals are assigned with respect to similar structure utilized in the dispensing system 20. The dispensing system 120 is characterized by curved side walls 122 of the first, second, third, and fourth wall portions 28, 66, 68, 72. The dispensing system 120 is also provided with a string 124 that is threaded through the hole 40. The string 124 may be used to support the dispensing system 120 from a support surface such as a rod or door knob. The present embodiment may also be provided without the cover 30 to omit material that has to be discarded. FIGS. 15 and 16 are illustrative of the variations that may be found in other embodiments with respect to the size and shape of various wall portions.

Figure 17:
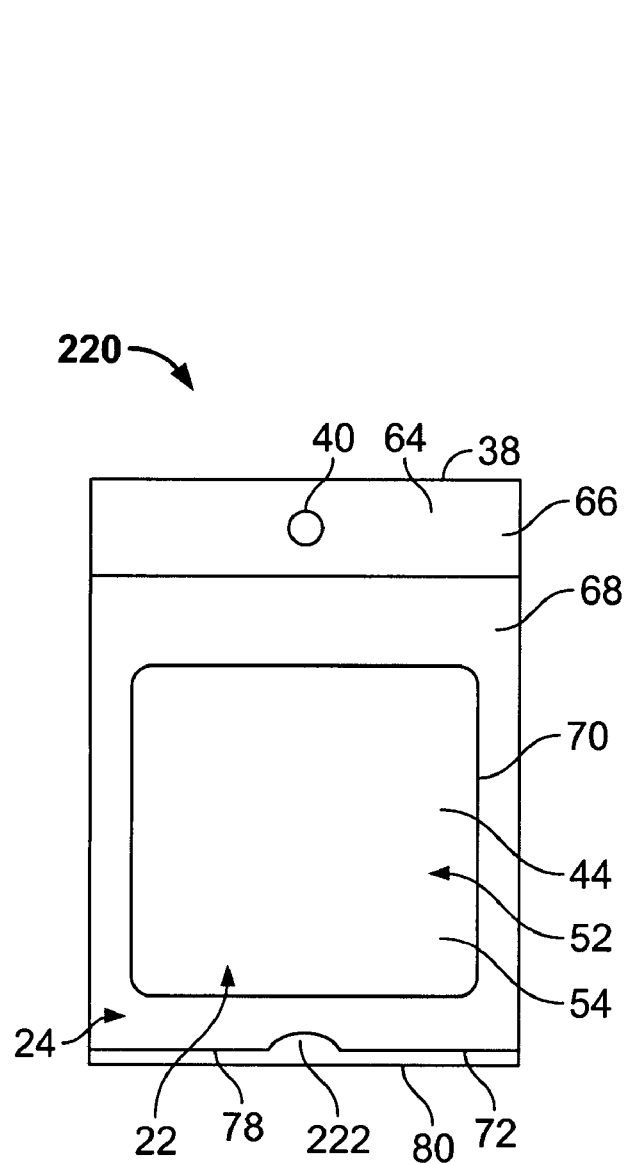
FIG. 17 is a rear elevational view of a third dispensing system in a first state that includes a frame and a dispenser.
Figure 18:
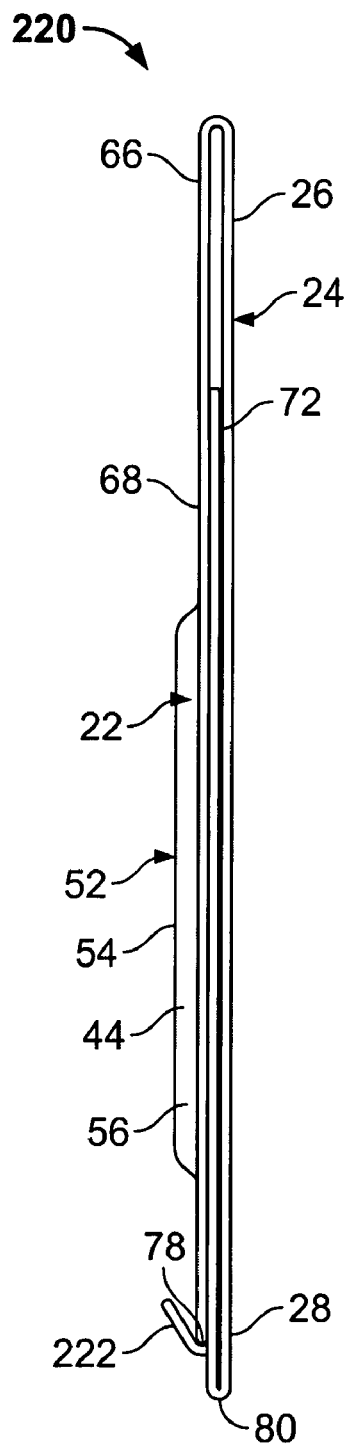
FIG. 18 is a side elevational view of the third dispensing system of FIG. 17.

FIGS. 17 and 18 depict a different embodiment of a dispensing system 220 similar to the dispensing system 20. However, the dispensing system 220 differs in that a retention member 222 is provided on the fourth wall portion 72 adjacent the bottom end 80 of the combined first and fourth wall portions 28, 72. The retention member 222 comprises a resilient curved member that is partially cut away from the fourth wall portion 72 and that is angled outwardly toward the third wall portion 68. When the dispensing system 220 is in the first state, a portion of the bottom end 78 of the third wall portion 68 is retained within the retention member 222. Retention of the third wall portion 68 within the retention member 222 causes the bottom end 78 of the third wall portion 68 to be held against the fourth wall portion 72. Removal of the third wall portion 68 from the retention member 222 transitions the dispensing system 220 from the first state to the second state. The retention member 222 provides the dispensing system 220 with enhanced means for maintaining the dispensing system 220 in the first state. For example, the retention member 222 may prevent an inadvertent state transition from an outside force acting on the dispensing system 220 or from movement of the third wall portion 68 due to over-flexing of the hinge 74. It is envisioned that other types of retention members may be used that are of varying shape, number, or placement. Further, a retention member may be integral with the display frame as shown with respect to FIGS. 17 and 18 or may be a separate structure attached to the display frame.

In a different embodiment, the dispensing systems 20, 120, 220 are provided with openings and dispensers of varying shapes. For example, the dispenser 22 and/or the cup-shaped structure 52 may be fashioned in the shape of a rectangle, circle, triangle, or other design, such as a snowflake or an animal. Further, multiple dispensers may be provided in a single dispensing system 20, 120, 220 with different or similar volatiles disposed therein. It is also envisioned that a re-usable adhesive may be used to hold some or all of the first, second, third, and fourth wall portions 28, 66, 68, 72 and the dispenser 22 together so that the dispenser 22 may be replaced as opposed to replacing the entire dispensing system 20, 120, 220 after the volatile material 58 has expired. In yet another embodiment, the dispensing systems 20, 120, 220 may be placed on a side thereof so that the bottom and top ends 36, 38 of the dispensing systems 20, 120, 220 do not touch a support surface. Rather, portions of the first, second, third, and fourth wall portions 28, 66, 68, 72 defining either a left or right side of the dispensing system 20, 120, 220 are disposed adjacent the support surface. The third wall portion 68 is still rotated about the hinge 74 to transition between first and second states and offers a user a different way of operating the present dispensing systems 20, 120, 220 as disclosed herein. Those skilled in the art will appreciate the numerous variations that may be made with respect to the present disclosure and which is intended to be captured by the present disclosure.

Figure 19:
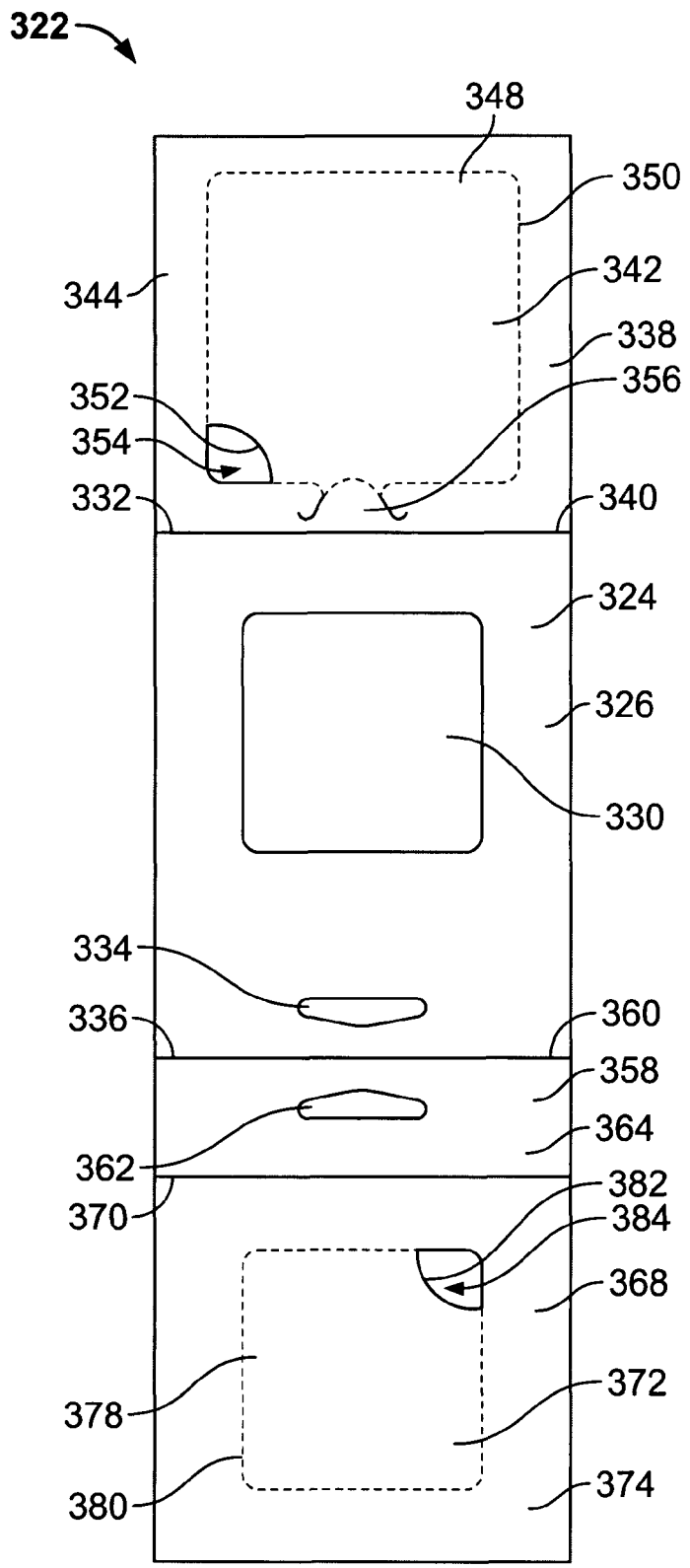
FIG. 19 is a plan view of a front side of a blank used to manufacture a fourth dispensing system.
Figure 20:
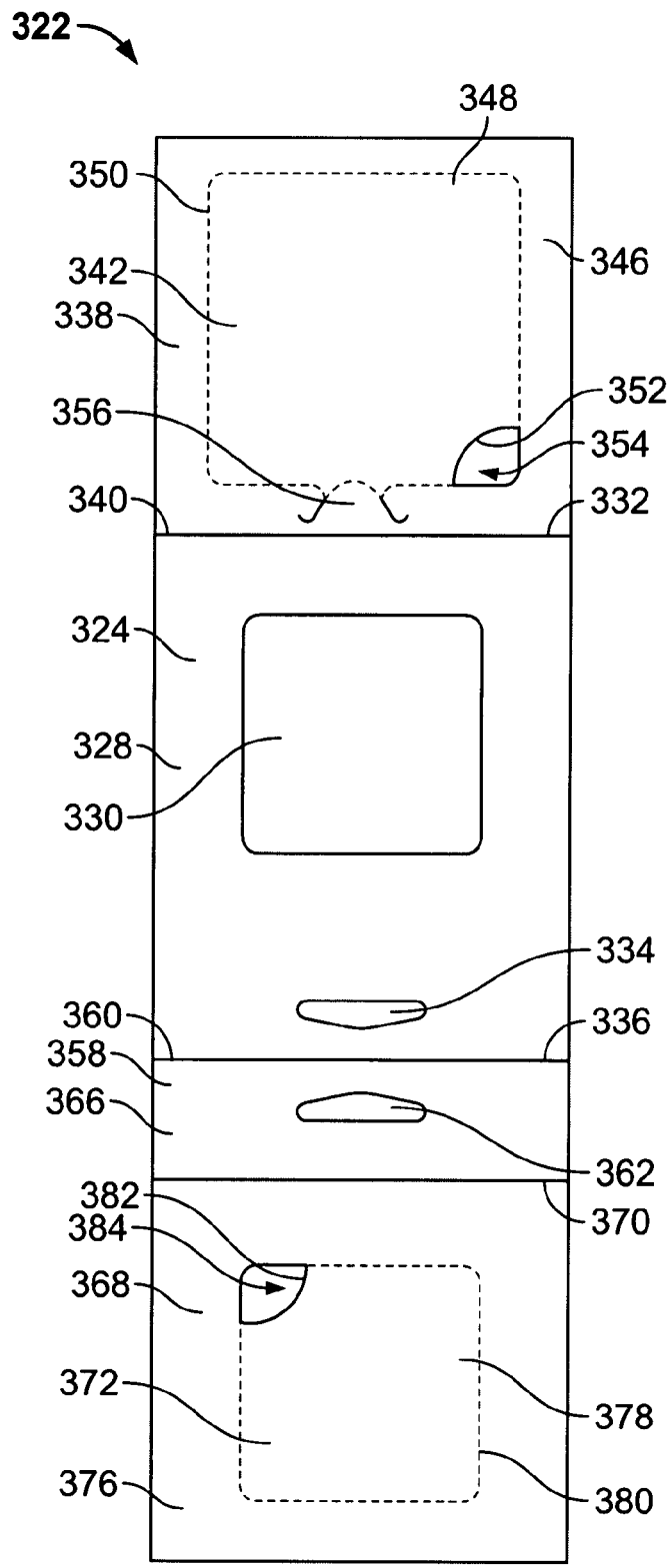
FIG. 20 is a plan view of a rear side of the blank of FIG. 19.

Referring now to FIGS. 19 and 20, yet another means for forming a volatile material dispensing system 320 (see FIGS. 21-28) is shown. In the present embodiment, the dispensing system 320 comprises a blank 322, which includes a first wall portion or segment 324 that has front and rear sides 326, 328, respectively. The first wall segment 324 is substantially rectangular in shape and has a width of about 4 in. and a height of about 5.2 in. A substantially square shaped first opening 330 is centered about a width of the first wall segment 324 and is disposed adjacent a first end or lower portion 332 thereof. The first wall segment 324 also includes a first hole 334 disposed adjacent a second end or upper portion 336 of the first wall segment 324. The first hole 334 has the shape of an obtuse triangle with curved corners. However, in other embodiments, the first hole 334 may comprise any other symmetrical or nonsymmetrical shape.

A second wall portion or segment 338 is attached to the first end 332 of the first wall segment 324 by a first hinge or fold line 340. The second wall segment 338 is substantially rectangular in shape and has a width of about 4 in. and a height of about 3.9 in. The second wall segment 338 also includes a second opening 342 and front and rear sides 344, 346, respectively. The second opening 342 is substantially square in shape and is centered about a width of the second wall segment 338. A first removable face or cover 348 is provided within the second opening 342 and is attached to portions of the second wall segment 338 defining the second opening 342 by a first perforated segment 350. The first cover 348 is substantially square except for an arcuately shaped portion 352 that has been removed from a corner of the first cover 348. The removed portion defines a first slot 354. In addition, a curved engagement or retention member 356 is provided proximate the first hinge 332. The engagement member 356 is defined by the first perforated segment 350 and slits on opposing sides thereof.

A third wall portion or segment 358 is attached to the second end 336 of the first wall segment 324 by a second hinge or fold line 360. The third wall segment 358 is substantially rectangular in shape and has a width of about 4 in. and a height of about 1.2 in. The third wall segment 358 includes a second hole 362 and front and rear sides 364, 366, respectively. The second hole 362 is disposed proximate the hinge 360 and is a mirror image of the first hole 334 about the hinge 360.

The blank 322 also includes a fourth wall portion or segment 368 attached to the third wall segment 358 at a third hinge or fold line 370. The fourth wall segment 368 is substantially rectangular in shape and has a width of about 4 in. and a height of about 3.8 in. The fourth wall segment 368 includes a third opening 372 and front and rear sides 374, 376, respectively. The third opening 372 is substantially square in shape and is centered about a width of the fourth wall segment 368. A second removable face or cover 378 is provided within the third opening 372 and is attached to portions of the fourth wall segment 368 defining the third opening 372 by a second perforated segment 380. The second cover 378 is substantially square except for a second arcuately shaped portion 382 that has been removed from a corner of the second cover 378. The removed portion defines a second slot 384.

In the present embodiment, the first and third openings 330, 372 are substantially square and have a height and width of about 2.3 in. However, in other embodiments the first and third openings 330, 372 may have different dimensions. Indeed, it is also envisioned that a non-square shape may be used in one or more of the first and third openings 330, 372. Further, the second opening 342 of the present embodiment is also substantially square but comprises larger height and width dimensions than the first and third openings 330, 372. For example, the second opening 342 of the present embodiment includes a height and width of about 2.9 in. Similarly, in other embodiments, other non-square shapes may be used for the second opening 342.

As described in more detail below, the size and shape of the first, second, and third openings 330, 342, 372, respectively, are adapted for use with the dispenser 22. For example, in the present embodiment the first opening 330 is adapted to receive the cup-shaped structure 52 of the dispenser 22 and preferably has a similar shape as the cup-shaped structure 52 and dimensions that are equal to or greater than the dimensions of the cup-shaped structure 52. As discussed above, the cup-shaped structure 52 can take on any symmetrical or non-symmetrical shape such as a rectangle, a circle, a triangle, a snowflake, or an animal. However, in other embodiments the first opening 330 may have a different shape than the cup-shaped structure 52 that is dimensioned to provide a large enough opening to allow the cup-shaped structure 52 to extend therethrough. Similarly, the second opening 342 has similar length and width dimensions as the peripheral flange 46 of the dispenser 22. In other embodiments, the second opening 342 is smaller or larger than the impermeable laminate 48 of the dispenser 22 or may comprise a different shape. However, it is contemplated by the present disclosure that the opening 342 provide access to the laminate 48 so that same may be easily removed from the dispenser 22. Finally, the third opening 372 can be any size and shape and is adapted to allow the volatile material 58 to diffuse from the dispenser 22 in a substantially uninterrupted manner. For example, the third opening 372 can be a similar shape as the permeable membrane 50 of the dispenser 22 and substantially aligned with the permeable membrane 50 to allow the volatile material 58 to diffuse uniformly through the third opening 372 when the dispensing system 320 is in the first state. Further, the size of the third opening 372 can be greater or lesser than the size of the permeable membrane 50 to provide greater or lesser obstruction, respectively, to the volatile material 58 as it diffuses into the environment, thereby controlling the diffusion of the volatile material 58.

FIGS. 21-28 depict how the blank 322 of the dispensing system 320 may be assembled into a display frame 386 for use in conjunction with the dispenser 22. The dispensing system 320 is assembled by inserting the cup-shaped structure 52 of the dispenser 22 (not shown in FIGS. 19 and 20) through the first opening 330 in the rear side 328 (see FIG. 20) of the first wall segment 324. The peripheral flange 46 of the dispenser 22 is adhered to portions of the first wall segment 324 that circumscribe an outer periphery of the first opening 330. The second wall segment 338 is rotated about the first hinge 340 to position the rear side 346 of the second wall segment 338 substantially flush with the rear side 328 of the first wall segment 324. The rear sides 328, 346 of the first and second wall segments 324, 338 are thereafter hot sealed together. The second wall segment 338 is positioned so that the impermeable laminate 48 of the dispenser 22 is generally centered behind the first cover 348 of the second wall segment 338. Similarly, the third wall segment 358 is folded about the second hinge 360 so that the rear side 366 thereof is substantially flush with the rear side 328 of the first wall segment 324, thereby allowing the first and third wall segments 324, 358 to be hot sealed together. The third wall segment 358 is positioned so that the second hole 362 thereof is aligned with the first hole 334 of the first wall segment 324. The rear side 376 of the remaining fourth wall segment 368 is provided in a substantially flush manner against the front side 344 of the second wall segment 338.

Figure 21:
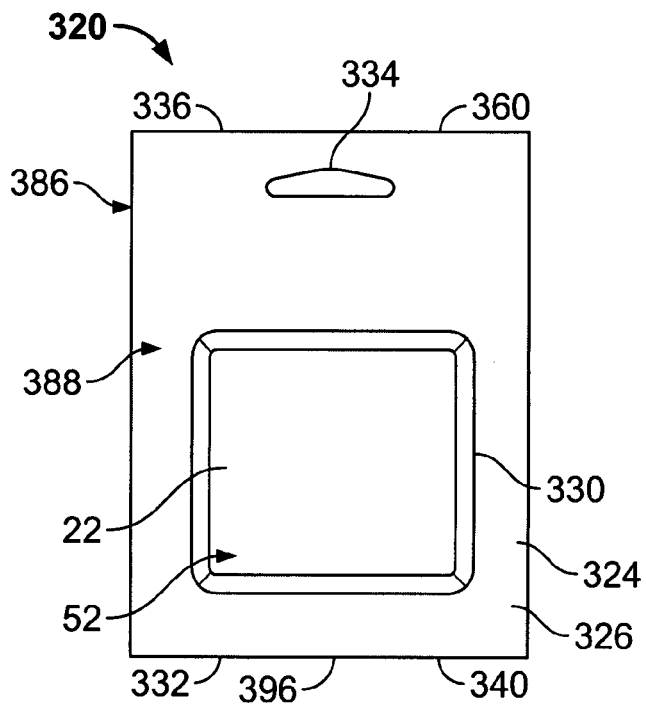
FIG. 21 is a front elevational view of the fourth dispensing system depicted in FIGS. 19 and 20 in a first state that includes a frame and a dispenser.
Figure 22:
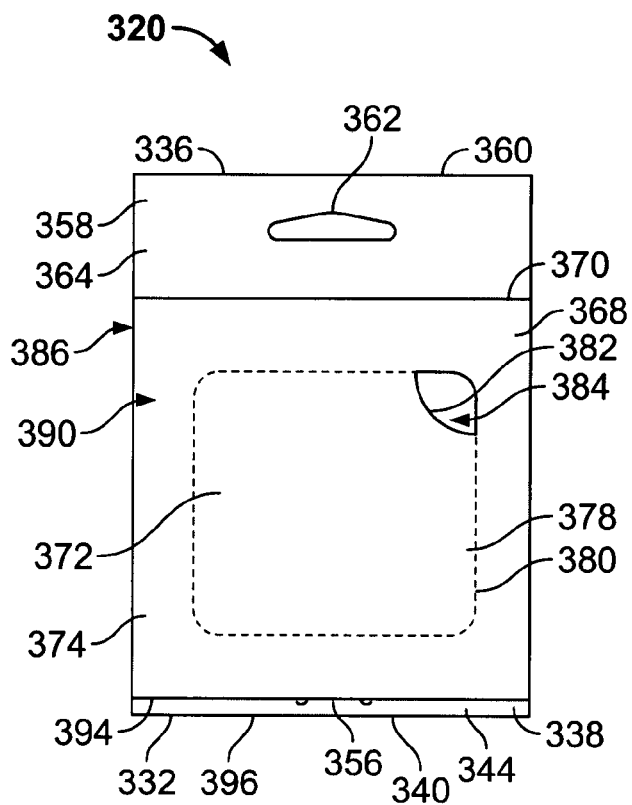
FIG. 22 is a rear elevational view of the dispensing system of FIG. 21.
Figure 27:
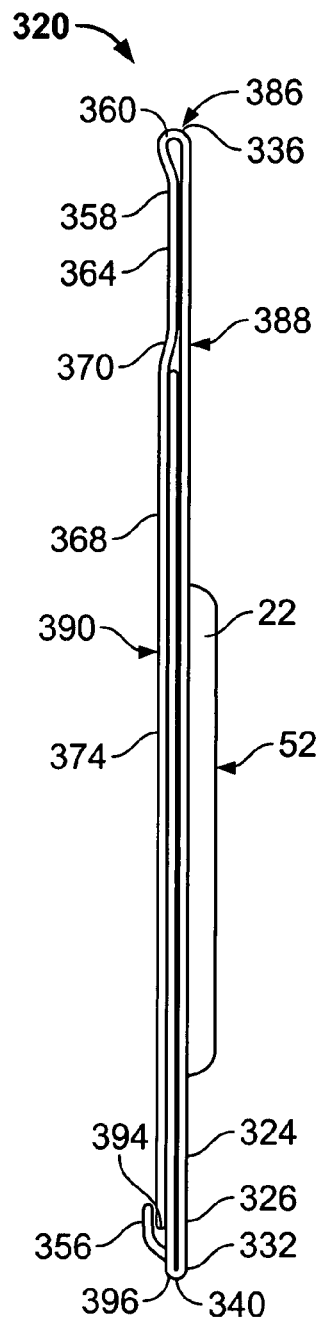
FIG. 27 is a side elevational view of the dispensing system depicted in FIGS. 21 and 22.

The dispensing system 320 is operable between first and second states similar to the embodiments described hereinabove. FIGS. 21, 22, and 27 show the dispensing system 320 in a first state. Turning to FIG. 21, a front face or segment 388 of the display frame 386 is shown, which includes the first wall segment 324, the first opening 330, and the first hole 334. The cup-shaped structure 52 of the dispenser 22 projects through the first opening 330. FIG. 22 depicts a back face or segment 390 of the display frame 386 that includes the third and fourth wall segments 358, 368. As noted above, the first and second holes 334, 362, respectively, are aligned to provide an opening therethrough, thereby allowing the dispensing system 320 to be placed on a display hook (not shown) and/or allow a string to be placed therethrough to hang the dispensing system 320 from a support structure. The back face 390 also includes the third opening 372 that is obstructed by the second cover 378.

Figure 23:
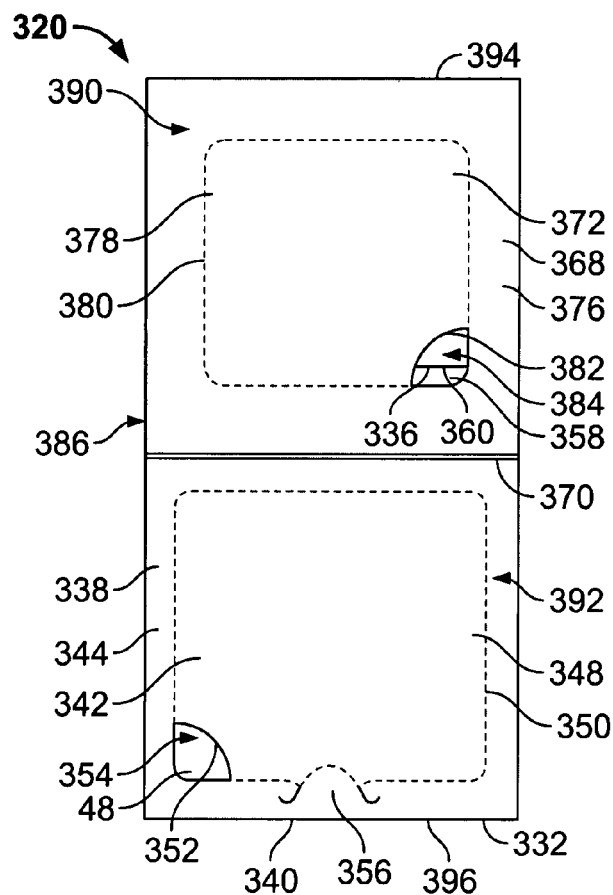
FIG. 23 is another rear elevational view of the dispensing system of FIG. 21 in a second state with a portion thereof folded upwardly.
Figure 24:
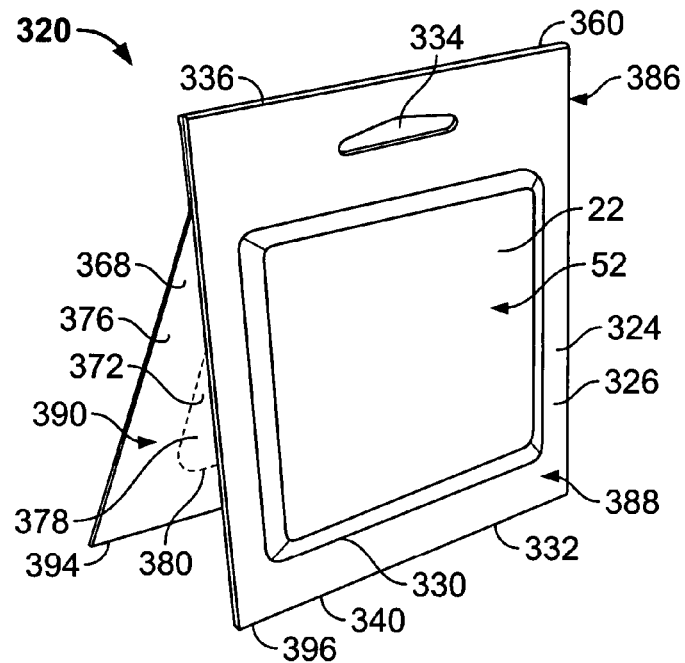
FIG. 24 is a front isometric view of the dispensing system of FIG. 21 in a second state.
Figure 25:
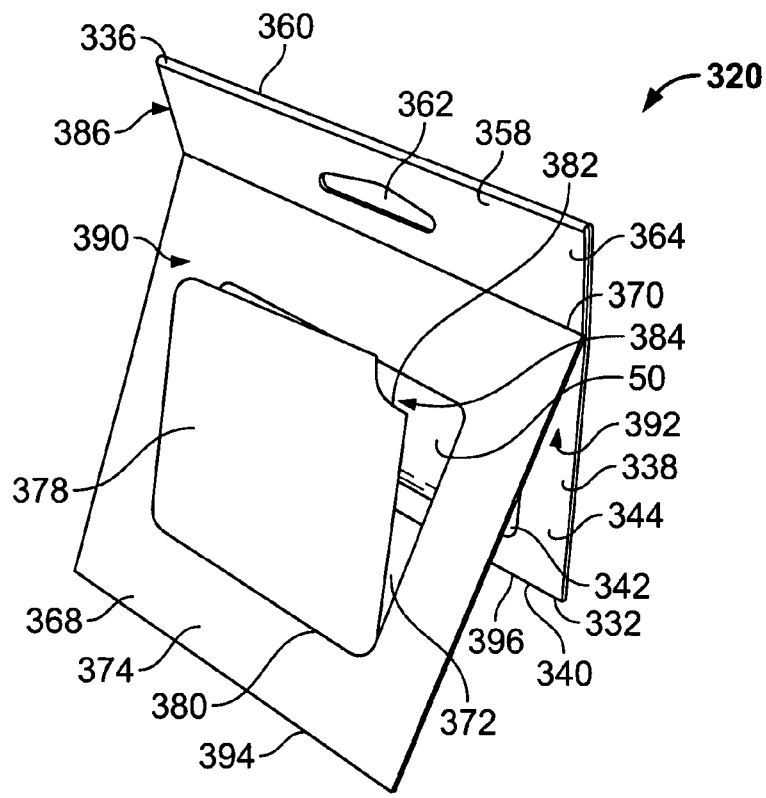
FIG. 25 is a rear isometric view of the dispensing system of FIG. 24.
Figure 26:
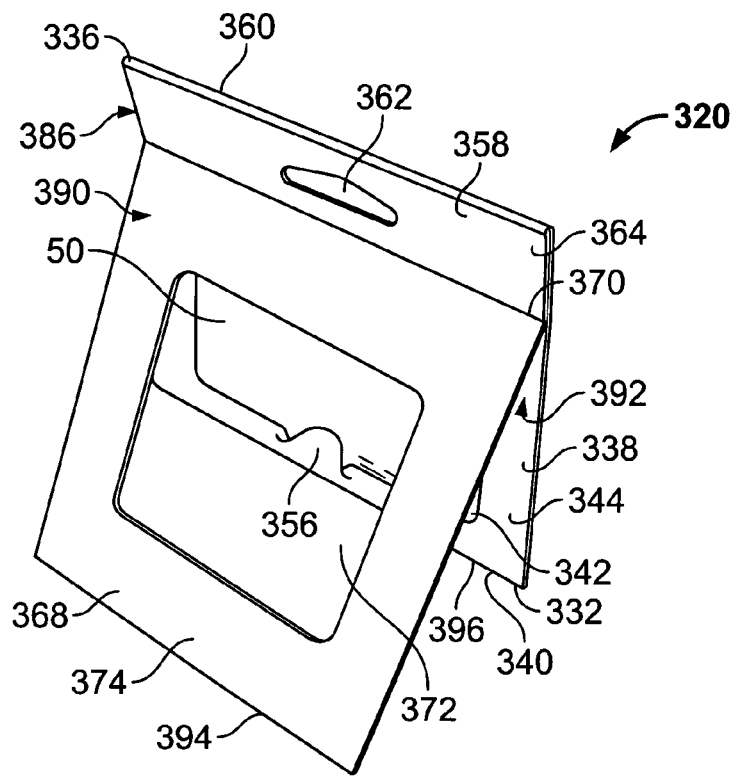
FIG. 26 is another rear isometric view of the dispensing system shown in FIG. 24, except that a cover has been removed.
Figure 28:
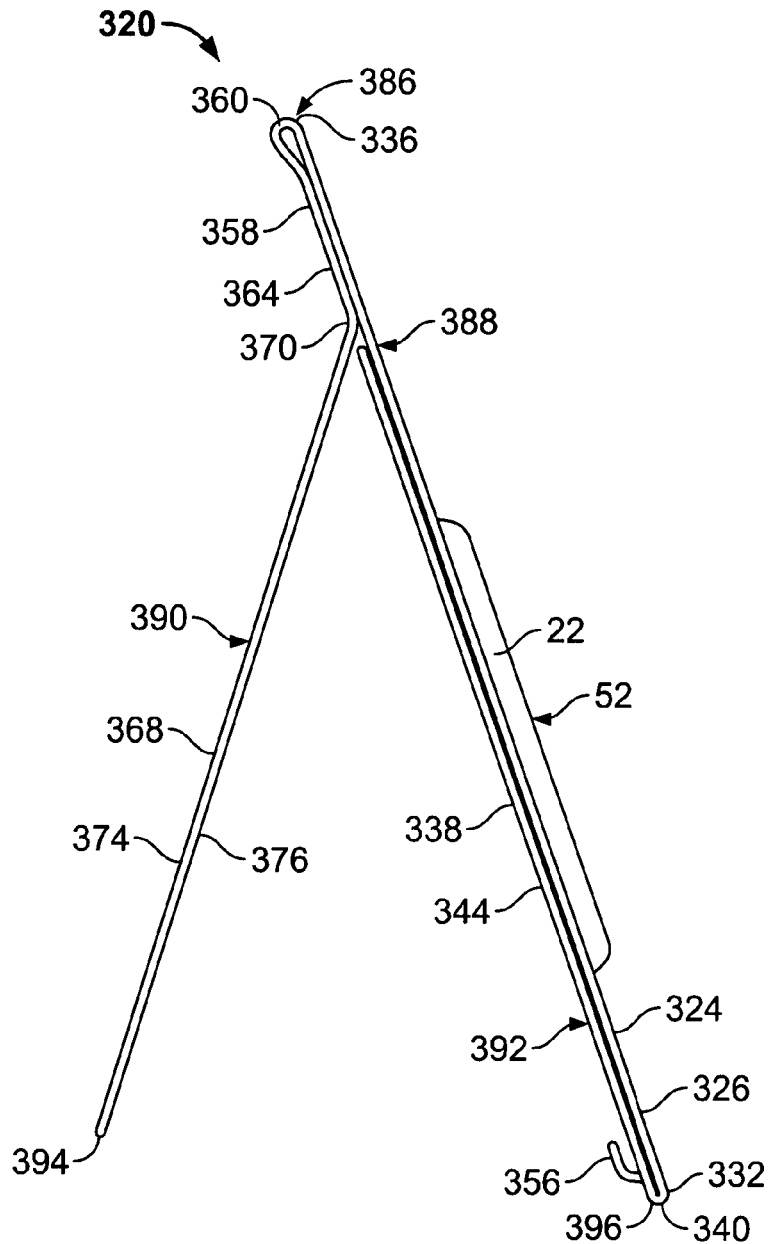
FIG. 28 is a side elevational view of the dispensing system of FIG. 26.

FIGS. 23-26 and 28 depict the dispensing system 320 in a second state. With particular reference to FIGS. 25 and 26, the back face 390 is shown. The dispensing system 320 is placed in the second state by rotating the fourth wall segment 368 about the hinge 370 and away from an intermediate face or segment 392, which comprises the second wall segment 338 and the second opening 342. In the second state, the third opening 372 is no longer in alignment with the second opening 342. The fourth wall segment 368 acts as a support member or foot member to assist in propping up the dispensing system 320 from a support surface (not shown). FIG. 28 illustrates that the dispensing system 320 takes on a substantially inverted V-shape in the second state with the third wall segment 358 and portions of the first wall segment 324 extending therefrom at an angle. A bottom end 394 of the fourth wall segment 368 and a bottom end 396 of the combined first and second wall segments 324, 338 exert forces upon the support surface to maintain the dispensing system 320 in an upright position in the second state. Similar to the other embodiments described herein, the fourth wall segment 368 is actuable between the first state and a plurality of positions that define the second state. The fourth wall segment 368 may be angled anywhere between about 1 degree to about 180 degrees with respect to the intermediate face 392 to place the dispensing system 320 in the second state. For example, FIG. 23 shows the intermediate face 392 of the display frame 386 with the fourth wall segment 368 rotated upwardly about the hinge 370 by an angle of about 180 degrees with respect to the intermediate face 392.

The dispensing system 320 may be placed into an operable position in either the first or second states. Turning to FIG. 23, the first and second covers 348, 378 are shown. The first cover 348 is removed by inserting at least one finger into the first slot 354 and pulling the first cover 348 away from the display frame 386, thereby separating the first cover 348 from the second wall segment 338 about the first perforated segment 350. Removal of the first cover 348 exposes the impermeable laminate 48 of the dispenser 22. The impermeable laminate 48 is removed from the dispenser 22 in a similar manner as described above to allow the volatile material 58 to diffuse through the permeable membrane 50. The second cover 378 is similarly removed by inserting at least one finger into the second slot 384 and pulling the second cover 378 away from the display frame 386 (see FIG. 25), thereby separating the second cover 378 from the fourth wall segment 368 about the second perforated segment 380. In another embodiment, the second cover 378 is removed and the first cover 348 and the impermeable laminate 48 are removable through the third opening 372. In some embodiments, the first and second covers 348, 378 are completely removed and separated from the display frame 386 and in other embodiments the covers 348, 378 are only partially removed and remain connected to the frame 386 along portions of the first and second perforated segments 350, 380, respectively. Consequently, the selective removal of the covers 348, 378 and the actuation of the dispensing system 320 between the first and second states provides diffusion control by increasing or decreasing obstructions to the volatile material 58 as it diffuses into the surrounding environment.

In the present embodiment, the removal of the first cover 348 along the first perforated segment 350 releases the engagement member 356 from the first cover 348. In a different embodiment, the engagement member 356 is provided separately from the first cover 348 and is not wholly or partially attached to same. As may be seen in FIG. 27, the engagement member 356 is adapted to retain the dispensing system 320 in the first state in a similar manner as the retention member 222 (see FIGS. 17 and 18) described above. More particularly, the bottom end 394 of the fourth wall segment 368 is retained by the engagement member 356 to keep the back face 390 substantially flush with the intermediate face 392.

Referring now to FIGS. 29-31B, additional embodiments of an upper portion 400 of the display frame 386 are shown. FIG. 29 depicts a small circular hole 402 that extends through the front and back faces 388, 390 of the display frame 386. A string or other member (not shown) may be provided through the hole 402 to hang the display frame 386. A larger circular opening 404 with a lateral slit 406 that similarly extends through the front and back faces 388, 390 of the display frame 386 is shown in FIG. 30. It will be apparent to one skilled in the art how the present embodiments may be utilized or modified to provide support to the display frame 386 in the first or second state. Indeed, in a different embodiment the fourth wall segment 368 is articulated approximately 180 degrees (see FIG. 23) and a door handle or other support structure is inserted into the third opening 372 (see FIG. 26). Alternatively, a lateral slit (such as the slit 406 in FIG. 30) is provided within the fourth wall segment 368 between the third opening 372 and an edge of the fourth wall segment 368 to allow the fourth wall segment 368 to hook onto a support structure.

FIGS. 31A and 31B show the front and back faces 388, 390, respectively, of a dispensing system 420 that includes a value added feature 422. In the present embodiment, the value added feature 422 is a removable hook 424. The removable hook 424 extends through an opening 426 similar to the first and second openings 334, 362 described above. Insertion of the removable hook 424 through the opening 426 allows the dispensing system 420 to be hung from a rod or other structure (not shown). The dispensing system 420 also includes a curved sidewall 428.

Figure 32:
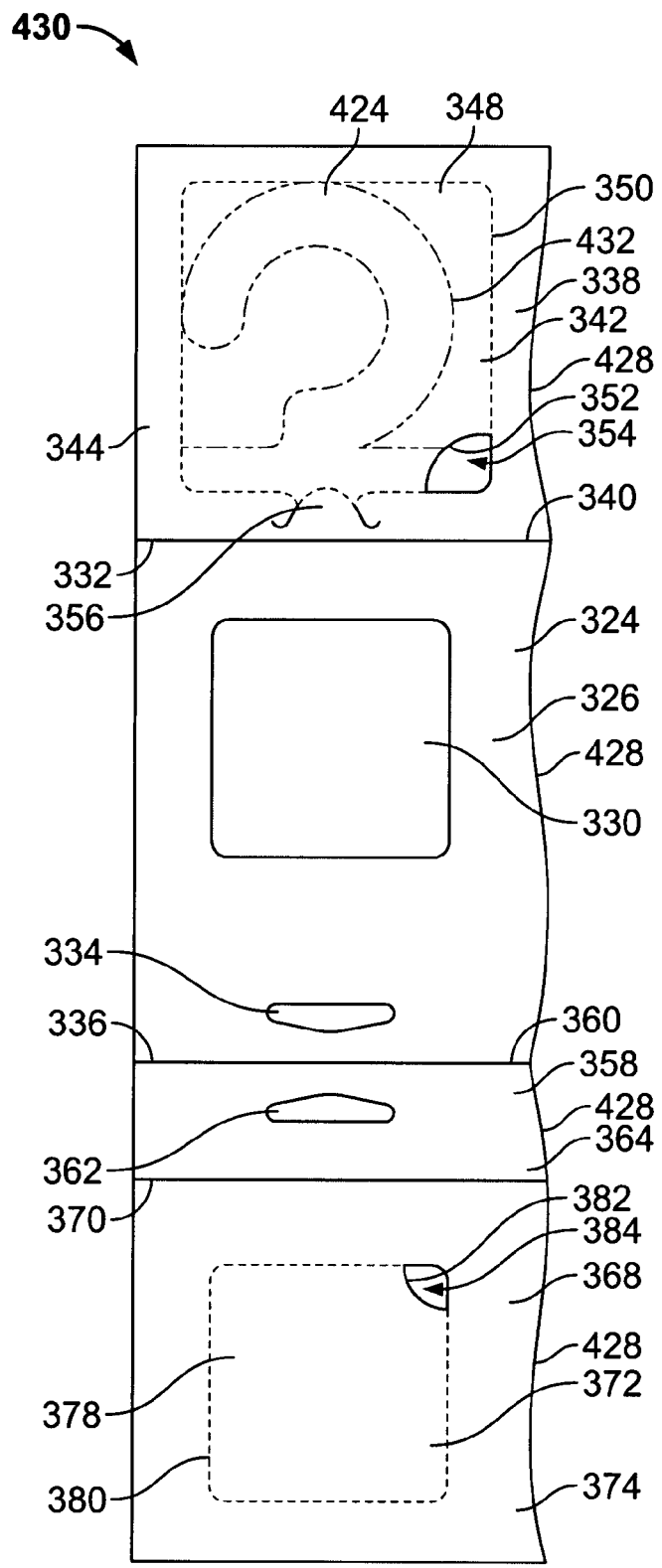
FIG. 32 is a plan view of a front side of a further embodiment of a blank used to manufacture the fourth dispensing system, similar to the blank shown in FIG. 19 except that the blank includes a contoured side and a perforated section for forming a hook.

FIG. 32 depicts a blank 430 adapted to be formed into the display frame 386 of the dispensing system 420. In fact, the blank 430 is identical to the blank 322 shown in FIGS. 19 and 20 except for the differences as noted hereinafter. The removable hook 424 is provided within the first cover 348 and is delineated by a third perforated section 432. In addition, each of the wall segments 324, 338, 358, 368 includes the curved sidewall 428. The blank 430 is otherwise folded and provided with the dispenser 22 in the same manner as the blank 322 to form the dispensing system 420 shown in FIGS. 31A and 31B. When the dispensing system 420 is desired to be placed in an operable condition, the first cover 348 is removed from the second wall segment 338 about the about the first perforated segment 350. Further, the removable hook 424 is removed from the first cover 348 about the third perforated section 432. The removable hook 424 may thereafter be inserted through the opening 426 to support the dispensing system 420 from a support structure. Such reuse of the first cover 348 reduces waste material and provides an added user-friendly feature to the dispensing system 420. In another embodiment, the removable hook 424 is disposed on the second cover 378.

Figure 33:
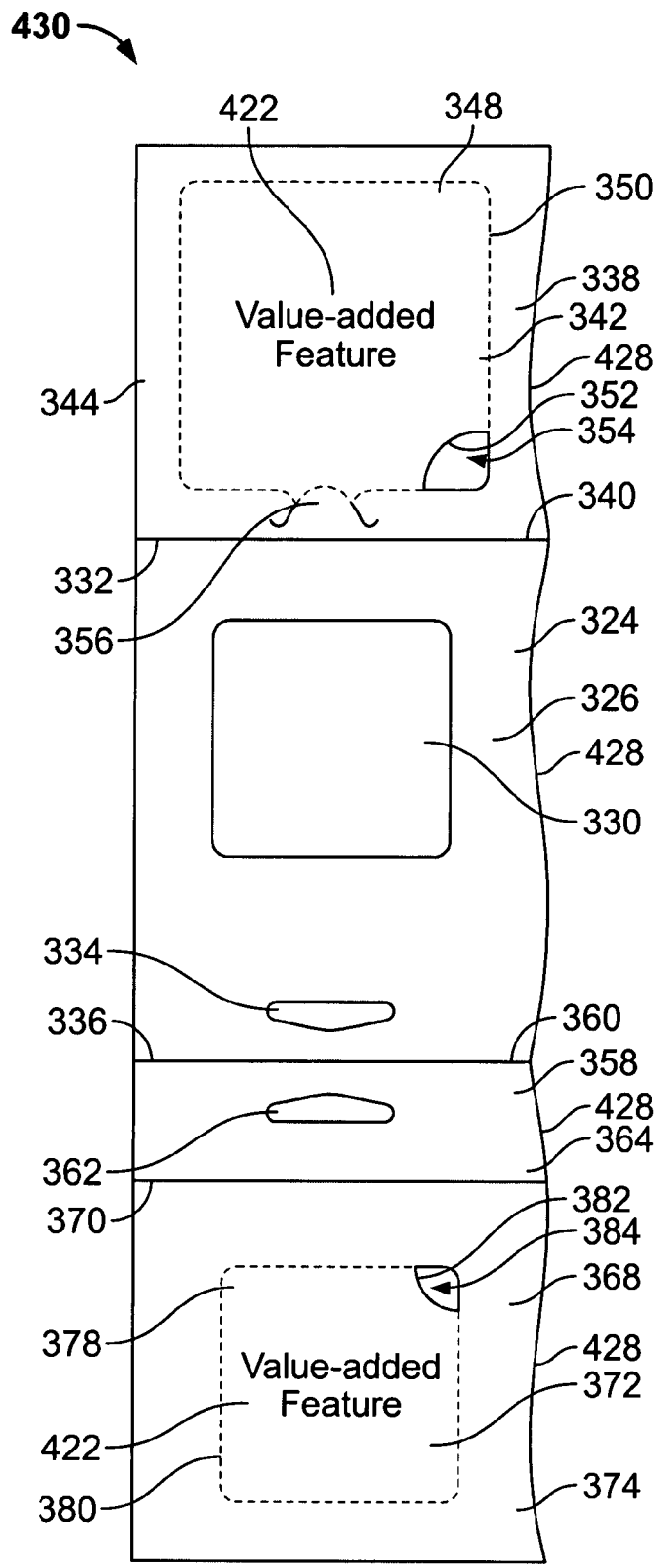
FIG. 33 is plan view of a front side of yet another embodiment of a blank similar to the one depicted in FIG. 32, except that the hook has been replaced by another value-added feature.

Other value-added features 422 may also be included with any of the dispensing systems disclosed herein. For example, the first and second covers 348, 378 may include branding, coupons for future purchases of the same or different products, user instructions, advertisements, decorative stickers, labels, adhesives to removably secure the dispensing system to support structures, and/or additional refill dispensers. In one embodiment, such as depicted in FIG. 33, the value added feature 422 is provided as part of one or more of the first and second covers 348, 378, respectively. However, the value added feature 422 may also be provided in any other suitable manner, e.g., as an additional insert or wall segment.

Other embodiments include all of the various combinations of individual features of each of the embodiments described herein.

INDUSTRIAL APPLICABILITY

The air freshener dispensing system described herein advantageously combines the functional and aesthetic characteristics of a display frame that is adjustable between a hanging position and a stand alone position with a fragrance dispenser. Thus, the use of the air freshener dispensing system provides a user greater flexibility in positioning an air freshener within a home or office setting.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A device adapted to discharge a volatile material, comprising:
   a display frame having a front face, a rear face, and an intermediate face;
   an opening disposed in the rear face, an opening disposed in the intermediate face, and a removable portion overlying the opening in the intermediate face; and
   a dispenser disposed within the display frame, wherein the dispenser comprises a blister holding a volatile material and a permeable membrane extending across an open end of the blister,
   wherein the rear face includes an integral foot member connected to an upper portion of the display frame at a hinge, and wherein the integral foot member is actuable between first and second states about the hinge, and
   wherein the permeable membrane is disposed adjacent the rear face and regulates and releases the volatile material therethrough in the first and second states.

2. The device of claim 1, wherein a removable portion overlies the opening in the rear face.

3. The device of claim 1, wherein an impermeable laminate is disposed substantially over the entirety of the permeable membrane to prevent the release of the volatile material, and wherein the impermeable laminate is at least partially removed from a portion of the permeable membrane to permit the release of the volatile material.

4. The device of claim 3, wherein the impermeable membrane is removable through the opening in the rear face when the integral foot member is in the first and second states.

5. The device of claim 1, wherein the dispenser is disposed between the front face and the intermediate face.

6. The device of claim 1, wherein an impermeable laminate is disposed substantially over the entirety of the permeable membrane to prevent the release of the volatile material, and wherein the impermeable laminate is at least partially removed from a portion of the permeable membrane through the opening in the intermediate face to permit the release of the volatile material.

7. The device of claim 1, wherein the integral foot member is substantially parallel with the front face in the first state and the integral foot member is angled from the front face in the second state.

8. The device of claim 7, wherein the display frame includes an engagement member that is adapted to secure the integral foot member in the first state.

9. The device of claim 7, wherein an impermeable laminate is disposed substantially over the entirety of the permeable membrane to prevent the release of the volatile material, and wherein the impermeable laminate is removable from a portion of the permeable membrane when the integral foot member is in the second state to permit the release of the volatile material.

10. The device of claim 1, wherein the front face includes an opening and the blister at least partially projects through the opening, and wherein the blister is adapted to allow a user to view an amount of the volatile material in the dispenser.

11. A dispensing system, comprising:
a frame having a front segment and a rear segment;
an opening disposed in the rear segment;
a dispenser disposed within the frame, wherein the dispenser comprises a blister holding a volatile material and a permeable membrane extending across an open end of the blister; and
a value-added feature included with the frame, wherein the value-added feature is a removable portion,
wherein the rear segment includes an integral foot connected to an upper portion of the frame at a hinge, and wherein the integral foot is actuable between first and second states about the hinge, and
wherein the permeable membrane is disposed facing toward the rear segment and releases the volatile material therethrough in the first and second states.

12. The system of claim 11, wherein the value-added feature is selected from the group consisting of branding, a coupon, an advertisement, user instructions, a detachable hook, a sticker, a label, an adhesive strip, and a dispenser refill.

13. The system of claim 11, wherein the value-added feature overlies the opening in the rear segment.

14. The system of claim 13, wherein the value-added removable portion is selected from the group consisting of branding, a coupon, an advertisement, user instructions, a detachable hook, a sticker, a label, an adhesive strip, and a dispenser refill.

15. The system of claim 11, further comprising an intermediate segment between the front segment and the rear segment, wherein the intermediate segment includes an opening and the value-added feature is a removable portion overlying the opening in the intermediate segment.

16. The system of claim 15, wherein the value-added removable portion includes a detachable hook.

17. The device of claim 15, wherein the value-added removable portion is selected from the group consisting of branding, a coupon, an advertisement, user instructions, a sticker, a label, an adhesive strip, and a refill.

18. A substantially flat blank adapted for assembly into a dispensing system, the blank comprising:
a first wall segment defining a first opening;
a second wall segment hingedly connected to a first end of the first wall segment about a first fold line, the second wall segment including a first removable face extending across a second opening;
a third wall segment hingedly connected to a second end of the first wall segment about a second fold line; and
a fourth wall segment hingedly connected to an end of the third wall segment about a third fold line, the fourth wall segment further including a second removable face extending across a third opening,
wherein the first and second openings are adapted to align with one another in an assembled state.

19. The blank of claim 18, wherein at least one of the first and second removable faces is a value-added feature.

\* \* \* \* \*